United States Patent
Stalter et al.

(10) Patent No.: US 12,343,207 B2
(45) Date of Patent: Jul. 1, 2025

(54) METHODS AND SYSTEMS FOR ULTRASOUND PROBE POWER MANAGEMENT

(71) Applicant: GE Precision Healthcare LLC, Wauwatosa, WI (US)

(72) Inventors: Ross Christopher Stalter, Waukesha, WI (US); Robert A. Meurer, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 276 days.

(21) Appl. No.: 18/058,224

(22) Filed: Nov. 22, 2022

(65) Prior Publication Data
US 2024/0164750 A1  May 23, 2024

(51) Int. Cl.
*A61B 8/00* (2006.01)
*H02J 50/10* (2016.01)

(52) U.S. Cl.
CPC ............ *A61B 8/4444* (2013.01); *H02J 50/10* (2016.02)

(58) Field of Classification Search
CPC ........... A61B 8/56; A61B 8/54; A61B 8/4405; A61B 8/4411; A61B 8/4427; A61B 8/4433; A61B 8/4444; H02J 2310/23; H02J 50/10; H02J 7/0044; B60R 2011/0071; F16M 11/04; H04M 1/04; H04M 1/06; H04M 1/02; H04B 1/3877
See application file for complete search history.

(56) References Cited

U.S. PATENT DOCUMENTS

| | | | | |
|---|---|---|---|---|
| 2005/0236545 A1* | 10/2005 | Seil | ...................... | B60R 11/0241 248/311.2 |
| 2008/0079388 A1* | 4/2008 | Sarnowsky | ........... | H02J 7/0042 320/108 |
| 2008/0169667 A1* | 7/2008 | Siniarski | ................. | B60R 7/082 296/37.8 |
| 2010/0314521 A1* | 12/2010 | Pauken | ................... | B60R 11/02 248/316.1 |
| 2019/0027953 A1* | 1/2019 | Rohmer | ................ | H02J 7/0044 |
| 2020/0266660 A1* | 8/2020 | Morrow | ................... | H02J 50/10 |
| 2020/0361355 A1* | 11/2020 | Chen | ...................... | B60N 3/103 |
| 2021/0085415 A1* | 3/2021 | Stalter | ................... | A61B 8/4405 |
| 2023/0225706 A1* | 7/2023 | Rahardja | .............. | A61B 8/4472 600/437 |
| 2024/0148362 A1* | 5/2024 | Knapp | ................. | A61B 8/4477 |

OTHER PUBLICATIONS

Stalter, R. et al., "Probe Cup," U.S. Appl. No. 29/868,180, filed Nov. 22, 2022, 11 pages.

* cited by examiner

*Primary Examiner* — Keith M Raymond
*Assistant Examiner* — Milton Truong
(74) *Attorney, Agent, or Firm* — McCoy Russell LLP

(57) ABSTRACT

Various methods and systems are provided for ultrasound imaging probe power management. In one embodiment, a charging system for a wireless ultrasound probe includes a base attachment configured to be removably coupled to an ultrasound system, a core charger configured to be removably coupled to the base attachment, and a probe holder. The probe holder is formed of a first bracket and a second bracket, wherein the first bracket is configured to be removably coupled to the core charger, and the second bracket is configured to receive the wireless ultrasound probe and position the wireless ultrasound probe adjacent to the core charger to enable charging of the wireless ultrasound probe via inductive charging.

20 Claims, 12 Drawing Sheets

METHODS AND SYSTEMS FOR ULTRASOUND PROBE POWER MANAGEMENT

TECHNICAL FIELD

Embodiments of the subject matter disclosed herein relate to ultrasound imaging, and more particularly, to a charging system for probes for ultrasound imaging.

BACKGROUND AND SUMMARY

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device. In some cases, wireless probes may be used to transmit data wirelessly to the ultrasound system, offering convenience and increased maneuverability for an operator of the probe.

Wireless ultrasound probes typically include a power source, such as a rechargeable battery which demands regular recharging. In one previous example, the probe may be placed on a wireless charging base on a table, for instance, at a location spaced away from the system or workstation. The location or placement of the probe may be unsecured or unstable, in some cases, and may be inconvenient for operators of the ultrasound imaging system, which may lead to delays in use of the probe. As such, a charging arrangement which allows the probe to be charged at a more convenient location, nearer the workstation, may be desired.

To resolve at least some of the aforementioned issues, the inventors have developed a modular wireless charging system configured to hold a rechargeable wireless ultrasound probe. A charging system includes a base attachment configured to be removably coupled to an ultrasound system, a core charger configured to be removably coupled to the base attachment, and a probe holder comprising a first bracket and a second bracket, wherein the first bracket is configured to be removably coupled to the core charger, wherein the second bracket is configured to receive the wireless ultrasound probe and position the wireless ultrasound probe adjacent to the core charger to enable charging of the wireless ultrasound probe via inductive charging. In this way, the charging system may be positioned on or near an ultrasound imaging system or workstation, so that the ultrasound probe may be conveniently charged at the workstation, greatly improving user experience and convenience.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to various embodiments for ultrasound imaging probe power management. In one example, an ultrasound imaging system includes a charging system removably coupled to a mounting attachment, the mounting attachment configured to couple to an element of the ultrasound imaging system. The charging system may be modular and include a core charger configured to charge rechargeable elements via inductive charging, a base attachment configured to be removably coupled to the core charger, and a probe holder configured to be removably coupled to the core charger and the base attachment. As will be elaborated on herein, each of the core charger, the probe holder, and the base attachment may include elements which allow quick and easy coupling and decoupling of the elements to each other without additional fasteners. Thus, the wireless charger can be easily disassembled (e.g., for maintenance) and may be assembled with a relatively small assembly time. The probe holder may have various different dimensions (e.g., size, shape, etc.) and configurations used to position and retain various ultrasound probes, and are not limited to the probe holders described herein. Further, the charging system may be easy to clean and may have few moving parts or joints, compared to conventional charging systems.

By configuring the charging system to be removably coupled to a mounting attachment and configuring the mounting attachment to be removably coupled to different elements of the ultrasound imaging system, a handheld ultrasound probe (e.g., wireless ultrasound probe) may be arranged more closely to an operator by seating the ultrasound probe in the charging system. As a result, an accessibility of the ultrasound probe may be increased. FIGS. 2-10 are shown approximately to scale, although other relative dimensions may be used, if desired.

Figure 1:
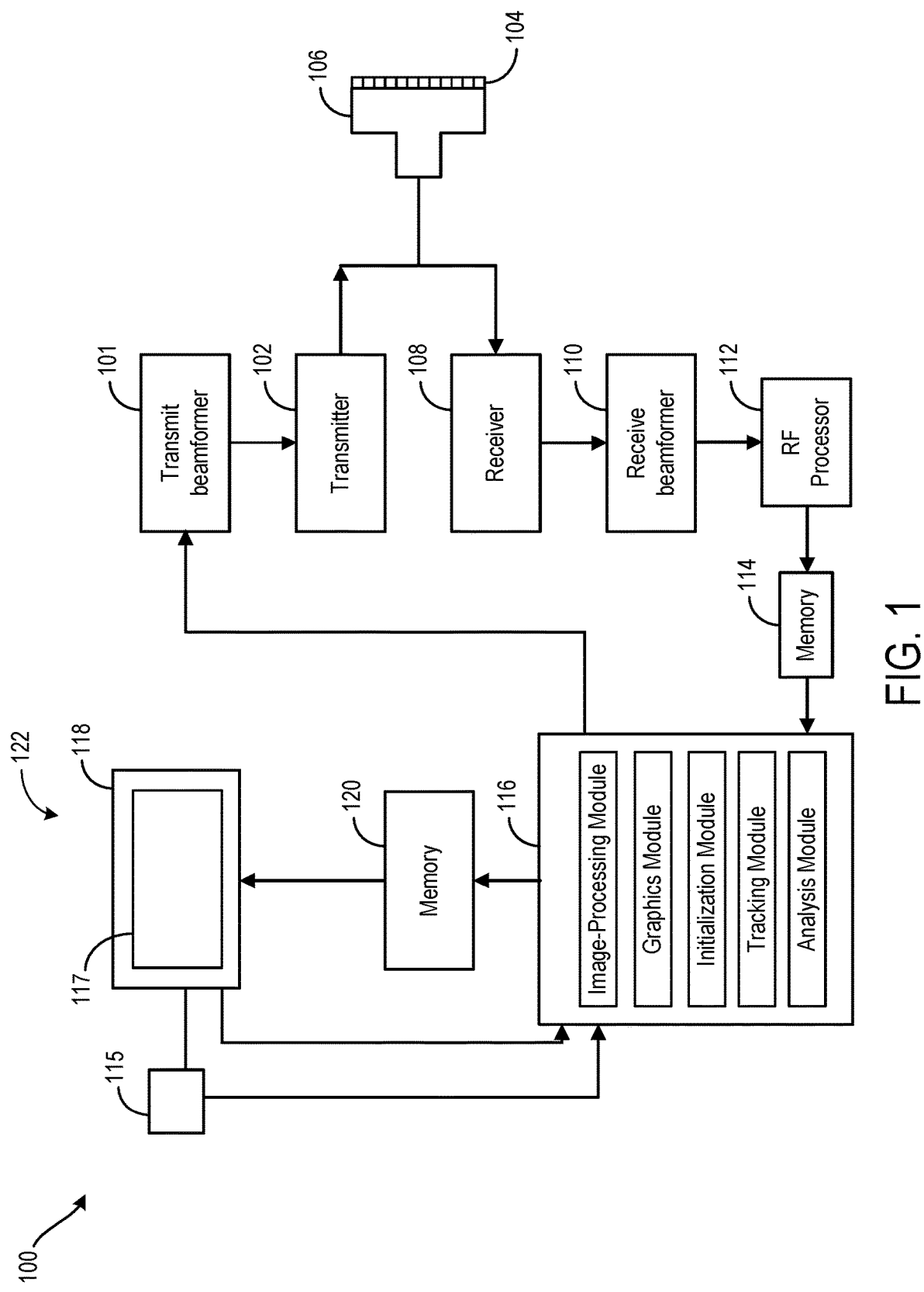
FIG. 1 schematically shows an ultrasound imaging system according to an embodiment of the disclosure.

FIG. 1 illustrates a block diagram of a system 100 according to one embodiment. In the illustrated embodiment, the system 100 is an imaging system and, more specifically, an ultrasound imaging system. As shown, the system 100 includes multiple components. The components may be coupled to one another to form a single structure in some examples. In some examples described herein, the system 100 may be a unitary system that is capable of being moved (e.g., portably) from room to room.

In the illustrated embodiment, the system 100 includes a transmit beamformer 101 and transmitter 102 that drives an array of elements 104 (e.g., piezoelectric crystals) within a diagnostic ultrasound probe 106 (or transducer) to emit pulsed ultrasonic signals into a body or volume (not shown) of a subject. The elements 104 and the probe 106 may have a variety of geometries. The ultrasonic signals are backscattered from structures in the body, such as blood vessels and surrounding tissue, for instance, to produce echoes that return to the elements 104. The echoes are received by a receiver 108. The received echoes are provided to a receive beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system 100 also includes a system controller 116 that includes a plurality of modules, which may be part of a single processing unit (e.g., processor) or distributed across multiple processing units. The system controller 116 is configured to control operation of the system 100. For example, the system controller 116 may include an image-processing module that receives image data (e.g., ultrasound signals in the form of RF signal data or IQ data pairs) and processes image data. For example, the image-processing module may process the ultrasound signals to generate slices or frames of ultrasound information (e.g., ultrasound images) for displaying to the operator. The image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the system controller 116) and displayed to the operator or user on a display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes the display device 118 having a display area 117. The display device 118 may be a touchscreen display that enables the operator to adjust operating parameters of the system 100 by directly interacting with (e.g., touching) the display device 118. For example, the display device 118 may be configured such that when a user moves a finger/glove/stylus across the face of the display device 118, a cursor atop the ultrasound image on the display area 117 moves in a corresponding manner. The display device 118 may detect a presence of a touch from the operator on the display area 117 and may also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the system controller 116 to the operator by displaying the information to the operator. The display device 118 and/or the user interface 122 may also communicative audibly. The display device 118 is configured to present information to the operator during the imaging session. The information presented may include ultrasound images, graphical elements, user-selectable elements, and other information (e.g., administrative information, personal information of the patient, and the like). In some embodiments, the user interface 122 may be additionally configured to interface with (e.g., electronically couple to) one or more user interface input devices 115, such as a physical keyboard, mouse, and/or touchpad.

In addition to the image-processing module, the system controller 116 may also include a graphics module, an initialization module, a tracking module, and an analysis module. The image-processing module, the graphics module, the initialization module, the tracking module, and the analysis module may coordinate with one another to present information to the operator during and/or after the imaging session. For example, the image-processing module may be configured to display an acquired image on the display device 118, and the graphics module may be configured to display designated graphics along with the ultrasound image, such as graphical outlines, which represent lumens or vessel walls in the acquired image. The image-processing and/or graphics modules within the system controller 116, may also be configured to generate a 3D rendering or image (not shown) of the entire vascular structure.

In some embodiments, the system controller 116 may also house an image-recognition module (not shown), which accesses stored images/videos (e.g., an image library) from either or both of the memory 114 and the memory 120, before analyzing them. For example, knowing the parameters under which a protocol is being carried out (ultrasound type, scan plane, tissue being imaged, etc.) the image recognition module may compare a live image on the display area 117, to one stored in memory 120, in order to analyze the image and thereby increase the accuracy of placing and utilizing analytical tools. In an alternative embodiment, instead of utilizing an image recognition module and image library, the system controller may house instructions for analyzing acquired imaging data (e.g., ultrasound images/videos acquired with the probe) and automatically determining a desired placement of one or more analytical tools, such as a region of interest.

The screen of the display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity, color flow velocity, texture, graininess, contractility, deformation, and rate of deformation value. The series of pixels then make up the displayed image generated from the acquired ultrasound data.

As described with respect to FIGS. 2-11, an ultrasound imaging system, such as the ultrasound imaging system (e.g., the system 100) of FIG. 1, includes a charging system configured to wirelessly charge a wireless ultrasound probe of the ultrasound imaging system. The charging system may be coupled to a mounting apparatus which is configured to mount (e.g., couple) the charging system on the ultrasound imaging system. As will be elaborated on herein, the charging system includes a base attachment configured to be removably coupled to the mounting apparatus, a core charger configured to be removably coupled to the base attachment and to charge the wireless ultrasound probe via inductive charging, and a probe holder configured to be removably coupled to the base attachment and the core charger and position the wireless ultrasound probe relative to the core charger such that the wireless ultrasound probe is retained in a position which enables inductive charging via the core charger. The probe holder may have various different dimensions (e.g., size, shape, etc.) and is not limited to the probe holders described herein. Coupling of the base attachment to the core charger and coupling of the probe holder to the base attachment and the core charger may be achieved through complementary geometry of each element of the charging system which enables quick, simple, and secure removable coupling, such as by snap-fitting elements together. The charging system is easy to clean and may be easily disassembled (e.g., for cleaning and/or maintenance) and may be assembled with a relatively small assembly time. The mounting apparatus may have various different dimensions (e.g., size, shape, etc.) configured to couple the charging system to the ultrasound imaging system, and is not limited to the mounting apparatuses described herein. By configuring the charging system as having modular elements which may be interchanged (e.g., different probe cup dimensions may be used with the core charger and the base attachment depending on a type of wireless ultrasound probe used), the charging system may be used with different ultrasound probes and mounted on different parts of the ultrasound system. The wireless ultrasound probe may be arranged more closely to an operator of the ultrasound imaging system by seating the wireless ultrasound probe against the core charger using the probe holder. As a result, an accessibility of the wireless ultrasound probe may be increased.

A first exemplary embodiment of a charging system is depicted in FIGS. 2-8. An axis system 201 is provided in FIG. 2 for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples.

Figure 2:
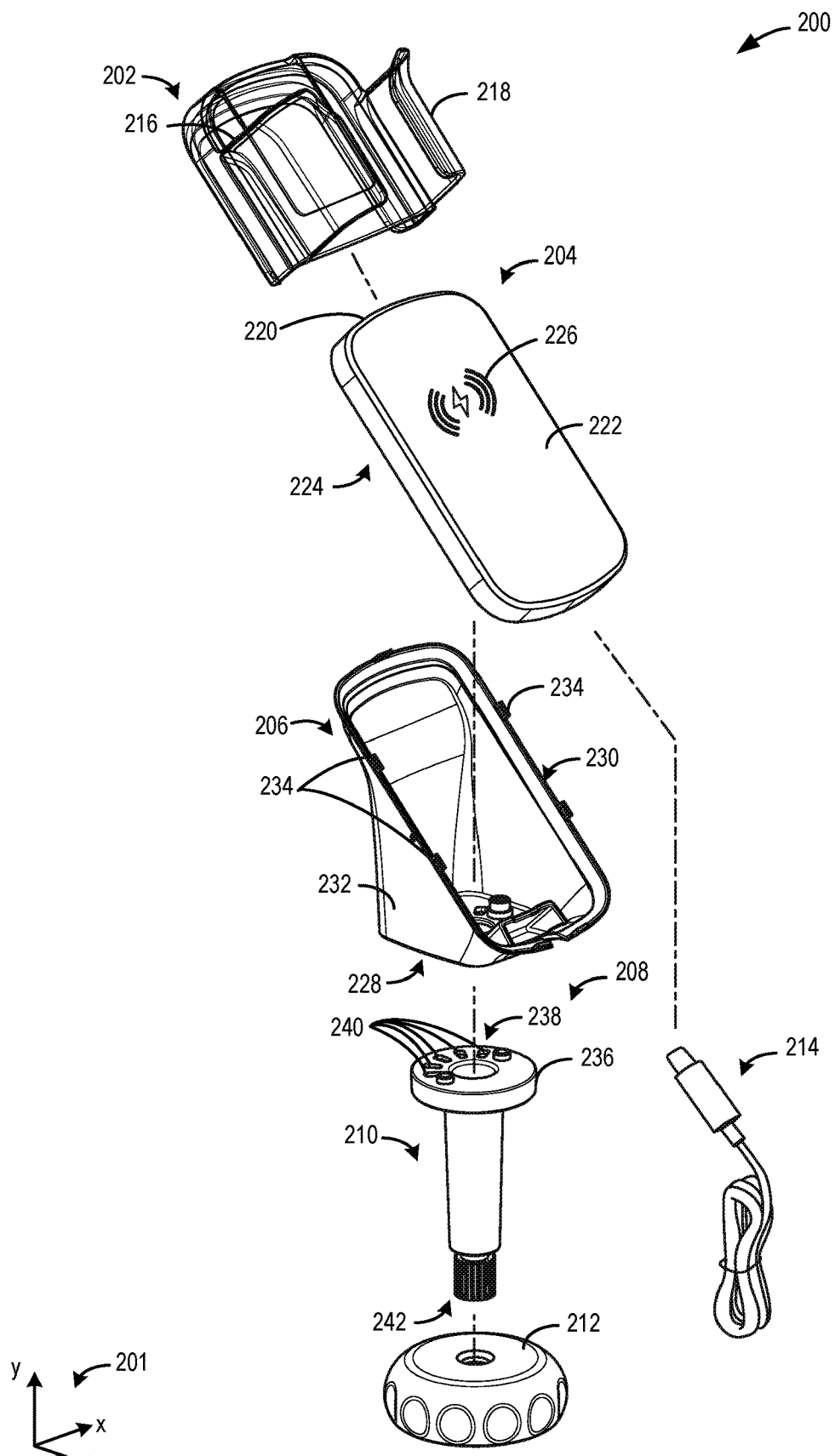
FIG. 2 shows an exploded view of elements of a charging system for a wireless ultrasound probe and a mounting attachment, according to an embodiment of the disclosure.

Turning to FIG. 2, a charging system 200 for a wireless ultrasound probe (e.g., the diagnostic ultrasound probe 106 of FIG. 1) is shown, according to a first exemplary embodiment of the disclosure. The charging system 200 includes a probe cup 202 (e.g., a probe holder), a core charger 204, and a base attachment 206. The core charger 204 may be configured to be removably coupled to the base attachment 206 and the probe cup 202 may be configured to be removably coupled to the core charger 204 and the base attachment 206. Further, a mounting attachment 208 may be coupled to the base attachment 206. As described with respect to the embodiment shown in FIG. 2, the mounting attachment 208 includes a mounting post 210 and a lock nut 212 which may be used to mount the charging system 200 on a medical imaging device, such as the ultrasound imaging system (e.g., the system 100) of FIG. 1. Additional exemplary embodiments of mounting attachments are described herein. A charging cable 214 may be plugged into the core charger 204 to provide power to the core charger 204, such as from a wall socket or power strip. For example, the charging cable 214 may be a USB, micro USB, USB-C and so on type connector.

As further described with respect to FIGS. 4 and 6-8, a wireless ultrasound probe may be seated against the core charger 204 to charge the wireless ultrasound probe. The probe cup 202 may retain and position the wireless ultrasound probe such that a rechargeable battery of the wireless ultrasound probe is aligned with a charging element of the core charger 204, allowing for wireless recharging of the wireless ultrasound probe. Further, the base attachment 206 may have an angled shape which positions the wireless ultrasound probe at an angle which simplifies access to the wireless ultrasound probe, compared to conventional charging systems. The base attachment 206 and the probe cup 202 may be formed in such a way that air may flow around the wireless ultrasound probe, e.g., between the core charger 204 and the wireless ultrasound probe, which may allow for heat management of the wireless ultrasound probe and the core charger 204. The base attachment 206 and the probe cup 202 described with respect to FIG. 2 are first exemplary embodiments of a probe cup and a base attachment which may be included in a charging system for a wireless ultrasound probe. Additional embodiments of a probe holder and a base attachment are described with respect to FIGS. 6 and 9-11. In this way, the charging system 200 may allow for heat management of the core charger 204 and the wireless ultrasound probe charged by the charging system 200, retention of the wireless ultrasound probe in the charging system 200, alignment of the rechargeable element of the wireless ultrasound probe with the charging element of the charging system 200, and modulation/adaptability of the charging system 200 to accommodate different wireless ultrasound probes, different mounting methods, and a plurality of use cases.

The probe cup 202 may be formed of a first bracket 216 and a second bracket 218, where the second bracket 218 extends outward from the first bracket 216. The first bracket 216 of the probe cup 202 may be positioned on the core charger 204 and the base attachment 206, when the core charger 204 and the base attachment 206 are coupled as described herein, by aligning an opening of the first bracket 216 with a first end 220 of the core charger 204 and sliding the first bracket 216 over the core charger 204 and the base attachment 206. The probe cup 202 may thus be quickly and easily releasably coupled to the core charger 204 and the base attachment 206 (e.g., as shown in an assembled configuration of the charging system 200 in FIGS. 6-8). In some embodiments, as further described with respect to FIGS. 3 and 5, each of the probe cup 202 and the base attachment 206 may be formed with additional features such as one or more protrusions and/or indentations so as to provide a snap-fit latching connection between the probe cup 202 and the base attachment 206, with the core charger 204 positioned therebetween. The snap-fit latching connection may provide an even more secure coupling between the probe cup 202, the core charger 204, and the base attachment 206, while still allowing easy and quick coupling and decoupling of the probe cup 202 therefrom, as desired. Together, the first bracket 216 and the second bracket 218 may retain the wireless ultrasound probe in the probe cup 202. For example, the second bracket 218 may extend at least partially around a portion of the wireless ultrasound prove. Additionally, when the probe cup 202 is coupled to the core charger 204 and the base attachment 206, the probe cup 202 may align the wireless ultrasound probe with a charging element of the core charger 204. Further detail of the probe cup 202 is described with respect to FIGS. 3A-3B.

The core charger 204 is an example of a wireless charger, wherein the core charger 204 may charge a wireless ultrasound probe via inductive charging. A wireless ultrasound probe may be positioned along a first surface 222 of the core charger 204 opposite a second surface 224 of the core charger 204, using the probe cup 202. The second surface 224 includes clip receivers, not shown in FIG. 2, which may be used to couple the core charger 204 to the base attachment 206, as further described with respect to FIGS. 4-7. A body of the core charger 204 (e.g., between the first surface 222 and the second surface 224) includes a charging element, not shown in FIG. 2, in an upper region of the core charger 204. A relative position of the charging element of the core charger 204 may be indicated by a charging symbol 226 in some examples. Further detail regarding position of the charging element of the core charger 204 is described with respect to FIG. 6, and further detail of the core charger 204 is described with respect to FIG. 4.

The base attachment 206 includes a bottom face 228, an angled face 230, and a hollow body 232. The bottom face 228 is a solid base which is continuous with the hollow body 232, and the angled face 230 is an angled plane which does not include a physical face continuous with the hollow body 232. The angled face 230 is angled at a non-zero angle relative to the bottom face 228 and includes a plurality of clip extensions 234 which may be used to couple the angled face 230 of the base attachment 206 to the second surface 224 of the core charger 204. In this way, the core charger 204 may be positioned at the angle of the angled face 230 of the base attachment 206, relative to the bottom face 228 of the base attachment 206. Further detail regarding the base attachment 206 is described with respect to FIGS. 5 and 6.

The mounting attachment 208 includes the mounting post 210 and the lock nut 212 which may be used to mount the charging system 200 onto a medical imaging device, such as the ultrasound imaging system (e.g., the system 100) of FIG. 1. The mounting post 210 may be coupled to the base attachment 206 by fitting a rim 236 formed at an upper end 238 of the mounting post 210 in face-sharing contact with the bottom face 228 of the base attachment 206 and threading screws through passages of the rim 236 and the bottom face 228. The rim 236 may include a plurality of vent slots 240 which may be aligned with vent slots of the bottom face 228 of the base attachment 206. Vent slots and passages of the bottom face 228 used to couple the base attachment 206 to the mounting attachment 208 are described with respect to FIG. 5. As shown in FIG. 2 and further described with respect to FIGS. 7A-8 and 10-11, the lock nut 212 of the mounting attachment 208 may be threaded onto a lower end 242 of the mounting post 210 to couple the lock nut 212 to the mounting post 210. When the mounting attachment 208 is coupled to the base attachment 206 and used to mount the charging system 200 onto an ultrasound device, a mount receiver of the ultrasound device may at least partially circumferentially surround the mounting post 210 and be positioned between the base attachment 206 and the lock nut 212, as described with respect to FIG. 8. As briefly described above, different embodiments of mounting attachments may be used to mount a charging system to an ultrasound device. Additional embodiments of mounting attachments are described herein.

Figure 3A:
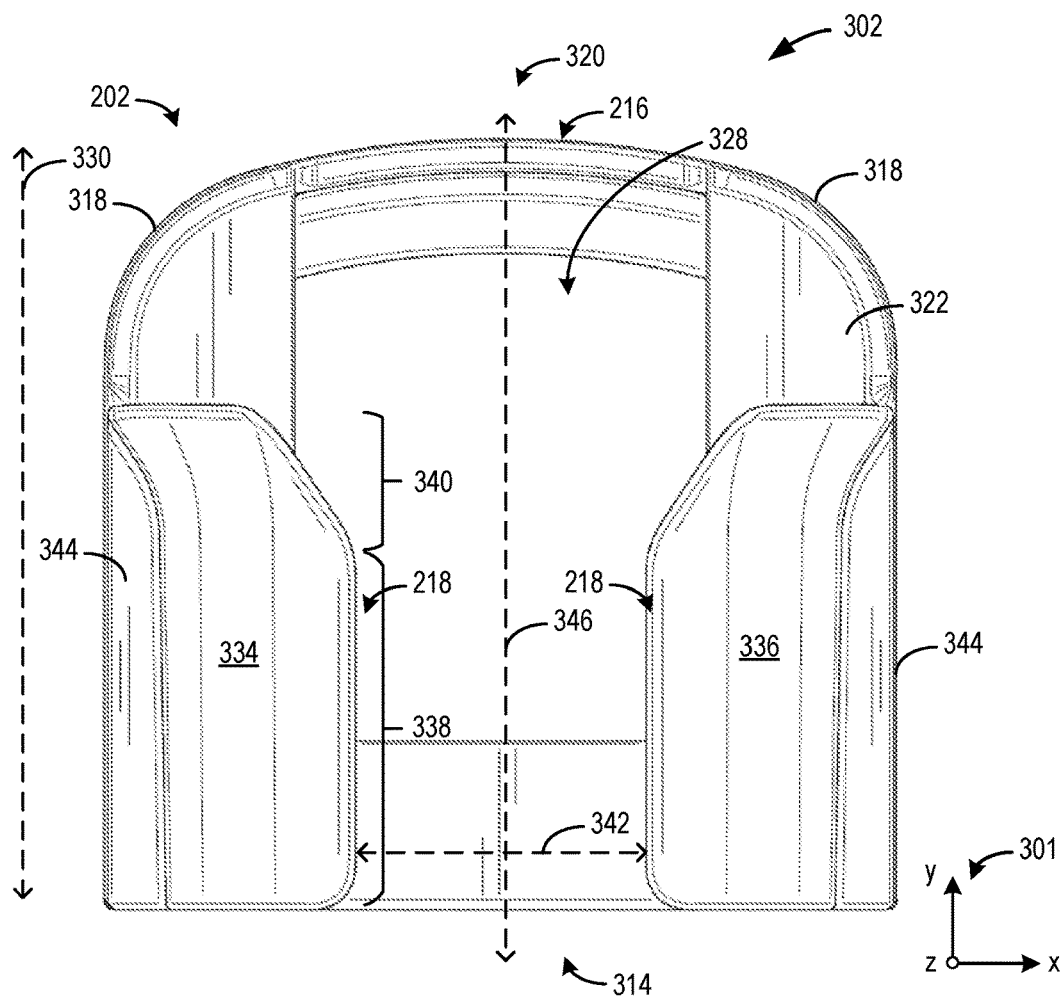
FIGS. 3A-3B show a plurality of views of a probe cup of the charging system of FIG. 2.
Figure 3A:
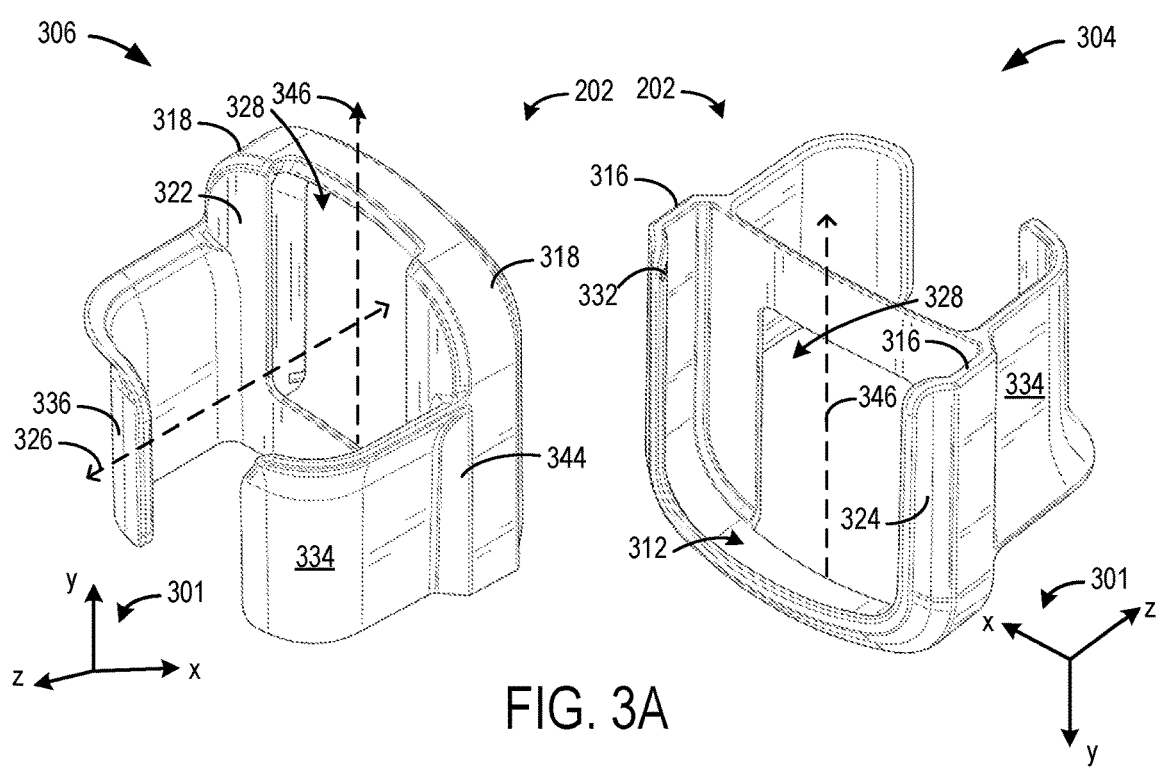
Figure 3B:
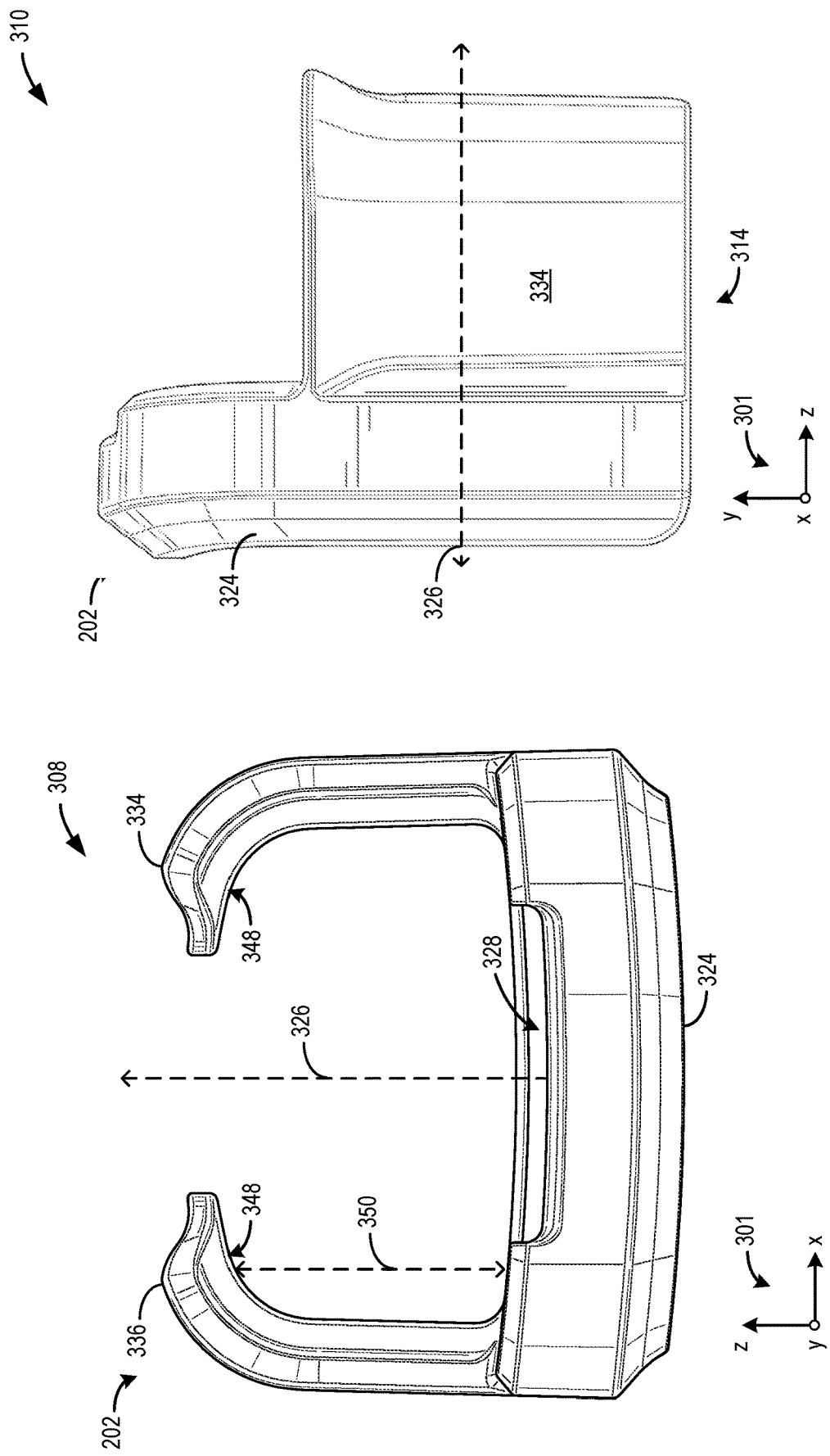

Turning to FIGS. 3A-3B, a plurality of views of the probe cup 202 of the charging system 200 of FIG. 2 are shown, including a front view 302, a bottom-rear-left perspective view 304, a front left perspective view 306, a top view 308, and a right side view 310. An axis system 301 is provided in FIGS. 3A-3B for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples.

Each of the plurality of views of FIGS. 3A-3B are herein described simultaneously. As described with respect to FIG. 2, the probe cup 202 includes a first bracket 216, which may be used to removably couple the probe cup 202 to the core charger 204 and the base attachment 206, and the second bracket 218, which may be used for retention and positioning of the wireless ultrasound probe. A first opening 312 of the first bracket 216 at a bottom 314 of the probe cup 202 is configured to receive the base attachment 206 and the core charger 204 (e.g., when the base attachment 206 is coupled to the core charger 204). For example, angled sidewalls 316 of the first opening 312 may be shaped to be complementary to a shape of the core charger 204 and the base attachment 206 when coupled together. The first opening 312 may be aligned with the first end 220 of the core charger 204, as described with respect to FIG. 2, and the first opening 312 of the probe cup 202 may slide over the first end 220 of the core charger 204, which is coupled to the base attachment 206.

Figure 4:
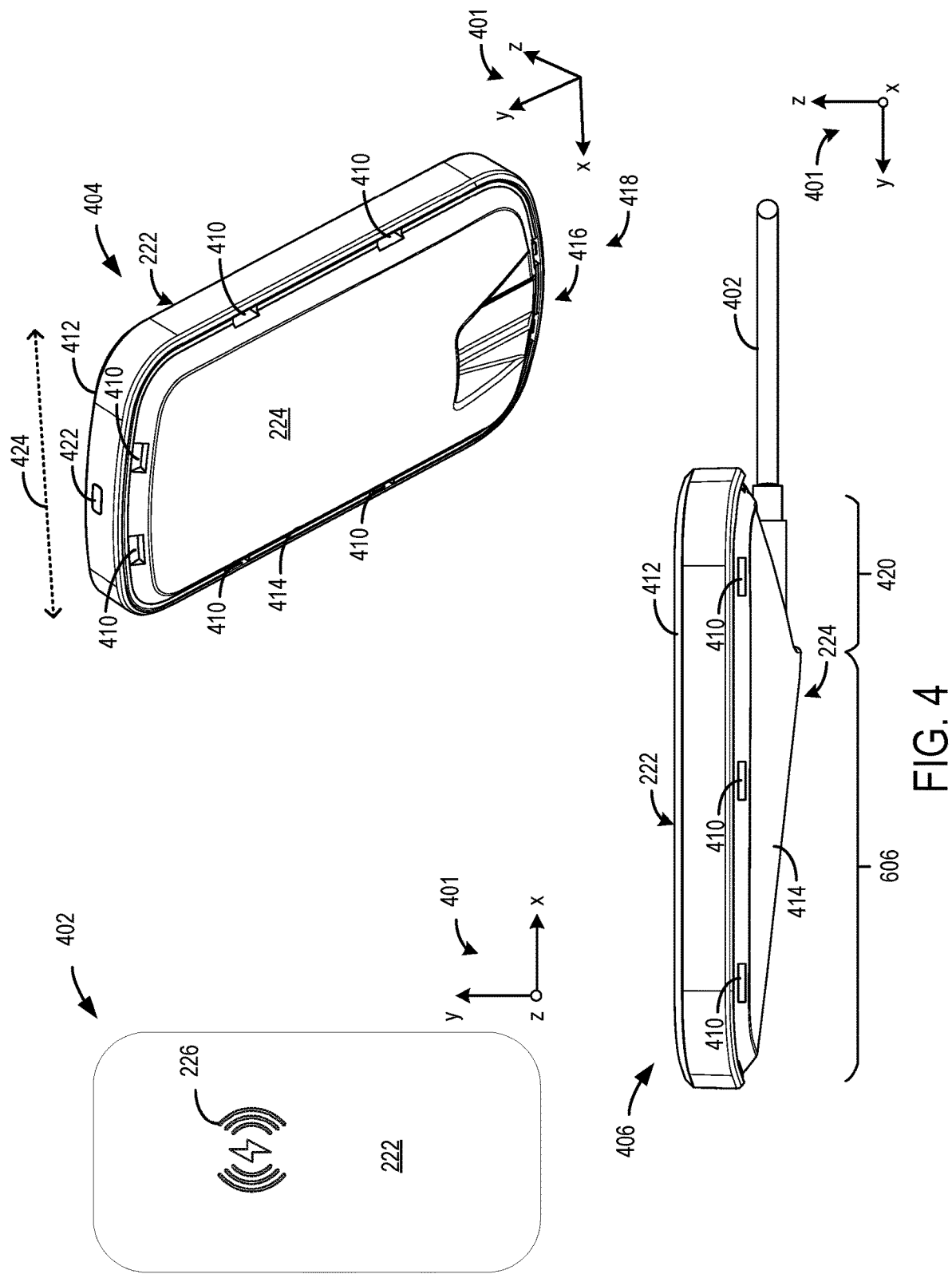
FIG. 4 shows a plurality of views of a core charger of the charging system of FIG. 2.

As described with respect to FIG. 2 and further described with respect to FIG. 4, the first end 220 of the core charger 204 may have curved edges. As shown in FIGS. 3A-3B, the first bracket 216 may also have curved edges 318 at a top 320 of the probe cup 202, opposite the first opening 312 at the bottom 314, where the curved edges 318 of the first bracket 216 are complementary to the curved edges of the first end 220 of the core charger 204, as further described with respect to FIGS. 6 and 7. In this way, the first bracket 216 of the probe cup 202 may slide over and rest on the first end 220 of the core charger 204, with assistance from gravity. For example, an interior face of the curved edges 318 of the first bracket 216 (e.g., continuous with the first opening 312) may be in face-sharing contact with the curved edges of the first end 220 of the core charger 204.

The first bracket 216 has a front face 322 from which the second bracket 218 extends. The front face 322 may be planar in some examples. A back face 324 of the first bracket 216 may be angled relative to the front face 322, for example, the back face 324 may angle away from the front face 322 (e.g., away from a plane parallel to the plane of the front face 322). The angle of the back face 324 may be complementary to an angle of the housing of the base attachment 206, as further described with respect to FIG. 5. In this way, the first bracket 216 may be slid over and at least partially surround the base attachment 206 and the core charger 204.

The first bracket 216 may have a stepped configuration which creates a standoff distance between the first surface 222 (e.g., the charging surface) of the core charger 204 and the front face 322 of the first bracket 216. For example, a cutout 328 extends from the top 320 of the first bracket 216 onto the front face 322 of the first bracket 216. In some examples, the cutout 328 may extend approximately three fourths of a length 330 of the probe cup 202. The cutout 328 may enable passive airflow between the core charger 204 and a wireless ultrasound probe positioned in the second bracket 218 of the probe cup 202 when the probe cup 202 is coupled to the core charger 204 as described herein. Passive airflow may at least partially cool at least one of the wireless ultrasound probe and the core charger 204. In some examples, operation of the core charger 204 (e.g., a charging ability) and the wireless ultrasound probe may be at least partially dependent on a temperature of the respective element. For example, if a temperature of the charging element of the core charger 204 exceeds a desired temperature, the charging element may be unable to provide charge to rechargeable elements (e.g., a battery of the wireless ultrasound probe) until the temperature decreases to the desired temperature. The standoff distance may thus enable heat from the core charger 204 and/or the wireless ultrasound probe to dissipate, which may increase a useable life of each element and may decrease a charging time.

The probe cup 202 may be positioned on and releasably coupled to the core charger 204 and the base attachment 206 by the complementary shapes of the first bracket 216 of the probe cup 202, and the core charger 204 and the base attachment 206. In this way, an operator may easily and quickly secure (e.g., latch) the probe cup 202 to the base attachment 206 and the core charger 204. Coupling of the probe cup 202 to the core charger 204 and the base attachment 206 may be further secured by at least one indentation 332 on each internal side of the first opening 312 of the first bracket 216. Each of the at least one indentation 332 may be complementary in size, shape, and position to a protrusion of the base attachment 206. Further detail describing protrusions of the base attachment 206 are described with respect to FIGS. 5 and 7. The at least one indentation 332 of the probe cup 202 and complementary protrusion of the base attachment 206 may provide a snap-fit latching connection between the probe cup 202 and the base attachment 206, with the core charger 204 positioned therebetween. The snap-fit latching connection may provide a more secure coupling between the probe cup 202, the core charger 204, and the base attachment 206, (e.g., compared to sliding the first bracket 216 of the probe cup 202 over the core charger 204) while still allowing easy and quick coupling and decoupling of the probe cup 202 therefrom, as desired.

The second bracket 218 extends from the front face 322 of the first bracket 216 and includes a first arm 334 and a second arm 336 configured to retain and position a wireless ultrasound probe positioned therein. Each of the first arm 334 and the second arm 336 of the second bracket 218 may be formed with the first bracket 216 such that the probe cup 202 is a continuous element. The first arm 334 and the second arm 336 may be similarly shaped with a linear extension 338 which extends approximately half of the length 330 of the probe cup 202 from the bottom 314 of the probe cup 202. Additionally, each of the first arm 334 and the second arm 336 may be inset from lateral edges 344 of the probe cup 202. The first arm 334 and the second arm 336 may be separated by a distance 342 therebetween.

The linear extension 338 of each of the first arm 334 and the second arm 336 curves towards a centerline 346 of the probe cup 202 such that a curvature 348 of each of the first arm 334 and the second arm 336 is complementary to a curvature of the wireless ultrasound probe. For example, a distance 350 between the curvature of first arm 334 and the front face 322 of the first bracket 216 is greater than a thickness of the wireless ultrasound probe, as further described with respect to FIG. 8. Each of the first arm 334 and the second arm 336 of the second bracket 218 flares outwards (e.g., away from the centerline 346 and a horizontal centerline 326 of the probe cup 202). An outward flare 340 of each of the first arm 334 and the second arm 336 may extend to the respective lateral edge 344 of the probe cup 202. A degree of curvature of the outward flare 340 may be complementary to a curvature of the wireless ultrasound probe, such that the wireless ultrasound probe rests against the outward flare of the first arm 334 and the second arm 336 and in face-sharing contact with the front face 322 of the first bracket 216 of the probe cup 202. The shape of the second bracket 218 is configured to, along with the force of gravity, retain the wireless ultrasound probe in a desired position (e.g., in the probe cup 202) and align the wireless ultrasound probe with the core charger 204 in such a way that a rechargeable element of the wireless ultrasound probe is aligned with a charging element of the core charger 204. Additionally, the second bracket 218 may be open on the bottom 314 of the probe cup 202, similar to the first opening 312 of the first bracket 216, such that a body of a wireless ultrasound probe positioned in the probe cup 202 may extend through the opening of the second bracket 218, as further described with respect to FIG. 8.

In some embodiments, the probe cup 202 is formed of a transparent material. For example, the transparent material may be a rigid or semi-flexible plastic. As further described with respect to FIGS. 7A-7B, the transparent material of the probe cup 202 may enable an indicator of the core charger 204 to be visualized through the probe cup 202 to indicate a charging status of a wireless ultrasound probe positioned in the probe cup 202 and therefore positioned adjacent to and charged by a charging element of the core charger 204. In some examples, the probe cup 202 may be formed of partially transparent material. In this or other examples, an interior surface (e.g., the first opening 312 and opposite the front face 322) may be etched or otherwise textured to enable diffusion of light throughout the probe cup 202 such that the light may be visible from multiple perspectives around the probe cup 202 (e.g., from a non-direct line of sight to the wireless ultrasound probe). In other examples, the probe cup 202 may not be formed of transparent material. For example, when the probe cup 202 is formed of fiber-reinforced plastic to increase a strength and rigidity of the probe cup 202, a surface of the probe cup 202 may be painted or otherwise covered with a non-transparent covering. This may create a desired visual aesthetic of the probe cup 202 and/or assist in locating the probe cup 202, such as in low-light conditions. When the probe cup 202 is formed of non-transparent materials, a transparent window or a cutout may be included in the top 320 of the probe cup 202, in linear alignment with the indicator of the core charger 204, allowing for visualization of the indicator when the probe cup 202 is positioned on (e.g., coupled to) the core charger 204.

Turning to FIG. 4, a front view 402, a rear right perspective view 404, and a right side view 406 of the core charger 204 are shown. An axis system 401 is provided in FIGS. 4 and 6 for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples. Each of the views of FIG. 4 are herein described simultaneously. As described with respect to FIG. 2, the core charger 204 includes the first surface 222 and the second surface 224, opposite the first surface. The first surface 222 may be a charging surface on which a wireless ultrasound probe may be positioned to recharge the wireless ultrasound probe.

Figure 6:
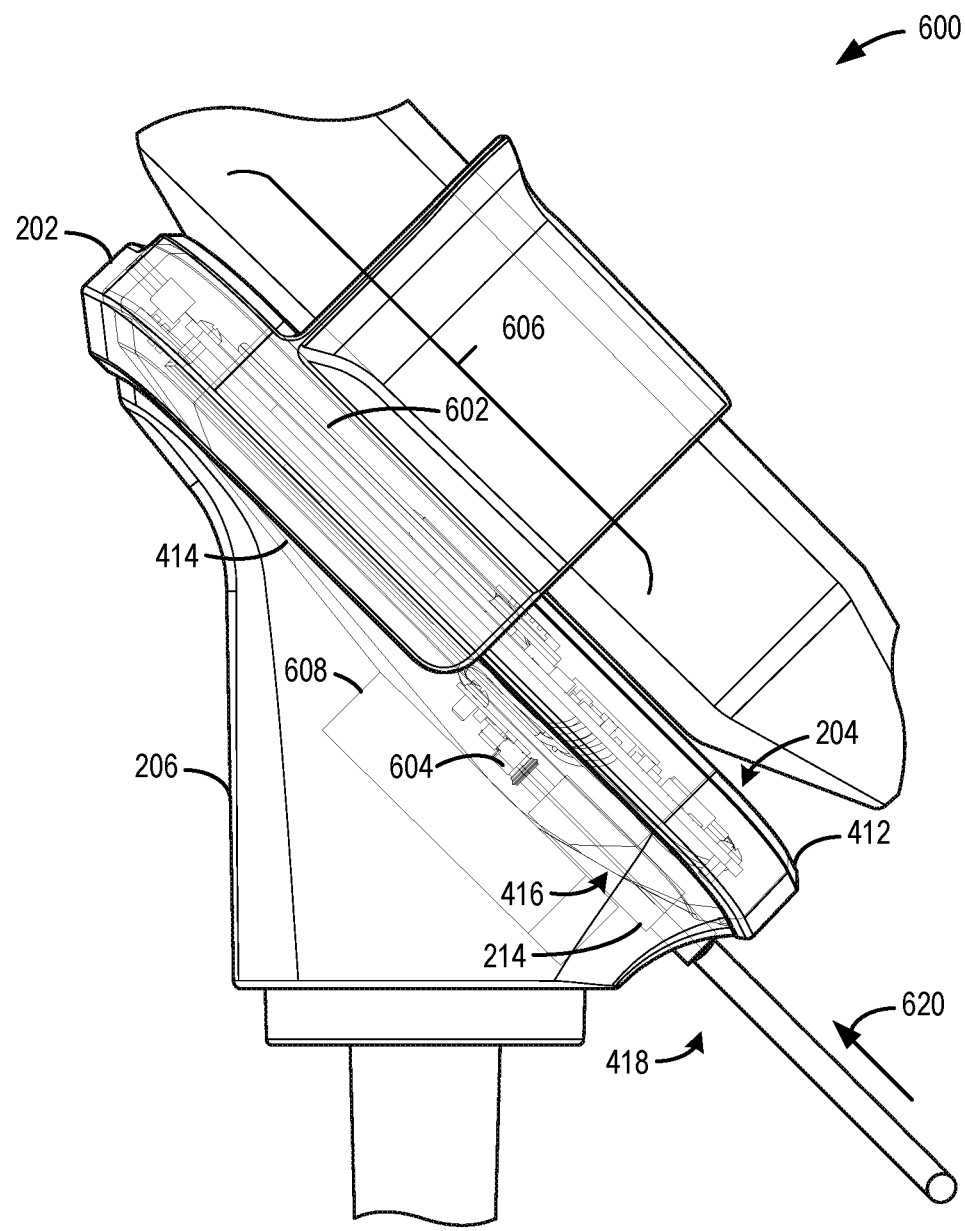
FIG. 6 shows a cross-sectional view of the charging system, according to an embodiment of the disclosure.

In some examples, the first surface 222 may be part of a front housing 412 of the core charger 204 and the second surface 224 may be part of a rear housing 414 of the core charger 204. The front housing 412 and the rear housing 414 may be coupled, as shown in FIG. 4, and have electronics positioned in a space therebetween. For example, turning briefly to FIG. 6, a cross-sectional view 600 of the probe cup 202, the core charger 204, and the base attachment 206 is shown. The core charger 204 includes a charging element 602, a charging port 604, and elements which connect the charging port 604 to the charging element 602 to power the charging element 602. The charging element 602 is positioned in an upper region 606 of the core charger 204 in some examples. As shown in FIGS. 2, 4, and 7, a relative position of the charging element 602 may be indicated on the first surface 222 by the charging symbol 226 or other indicator. As shown in FIG. 6, the charging element 602 is configured to charge rechargeable elements, such as a battery of the wireless ultrasound probe, via inductive charging. For example, inductive charging is a type of wireless power transfer which uses electromagnetic induction to provide electricity to a device. As described herein, the charging element 602 provides electricity to the battery of the wireless ultrasound probe. The charging element 602 and the wireless ultrasound probe may each include an induction coil. Alternating current which passes through the induction coil of the charging element 602 may create a magnetic field which fluctuates in strength due to fluctuation in amplitude of the current. The fluctuation of the magnetic field creates an alternating current in the induction coil of the wireless ultrasound probe, which in turn may pass through a rectifier to convert it to direct current. The direct current may charge the battery of the wireless ultrasound probe and/or directly provide operating power to the wireless ultrasound probe. The charging port 604 is configured to receive a charging cable (e.g., the charging cable 214 of FIG. 2), which may be plugged into a wall socket or other power source to provide power (e.g., alternating current) to the charging element 602 of the core charger 204.

Returning to FIG. 4, the rear housing 414 of the core charger 204 includes a plurality of clip receivers 410, which may be equally spaced along a perimeter of the rear housing 414. The plurality of clip receivers 410 are positioned at locations and angles along the perimeter of the rear housing 414 in a way that enables coupling of the core charger 204 to a base attachment (e.g., the base attachment 206 of FIG. 2 and further described with respect to FIG. 5) by inserting the plurality of clip extensions 234 of the base attachment 206 into the plurality of clip receivers 410 of the core charger 204. As shown in FIG. 6, the rear housing 414 further includes an opening 416 at a second end 418 of the core charger 204 via which a charging cable (e.g., the charging cable 214 of FIG. 2) may be plugged into the charging port 604. Returning to FIG. 4, the second surface 224 of the rear housing 414 may be angled away from the first surface 222 moving from the upper region 606 to a lower region 420 of the core charger. As shown in FIG. 6, the lower region 420 of the rear housing 414 may extend to partially cover the opening 416, such that the charging port 604 is accessible from a direction indicated by an arrow 620. In addition to the base attachment 206, this may reduce debris, such as dust and other particles, from entering the charging port 604 and decreasing an ability of the charging port 604 to retain the charging cable 214.

The core charger 204 may further include a detector and an indicator which identifies and indicates a charging status of a wireless ultrasound charger positioned on the core charger 204 (e.g., positioned in the probe cup 202 coupled to the core charger 204). In the example shown in FIG. 4, the core charger 204 includes an LED 422 at the first end 220 of the core charger. The LED 422 may be centered along a width 424 of the core charger 204. As described with respect to FIGS. 3A-3B and further described with respect to FIGS. 7A-7B, when the probe cup 202 is formed of transparent material, the LED 422 of the core charger 204 may be visualized through the top 320 of the first bracket 216 of the probe cup 202 when the probe cup 202 is positioned on the core charger 204. In other configurations, the core charger 204 may additionally or alternately include edge lighting to indicate the charging status of the wireless ultrasound charger. The edge lighting may extend about a perimeter of the first surface 222 and/or the second surface 224, in some examples, which may enable visualization of the charging status from different positions with respect to the charging system 200.

The LED 422 may provide indication of a charging status by emitting different colored light and different light patterns, in some examples. When the wireless ultrasound probe is not positioned on the core charger 204 (e.g., positioned by the probe cup 202) and the core charger 204 is on (e.g., plugged into a power source via the charging cable 214), an indicator light may be shown continuously to indicate the core charger 204 is ready to charge. When the wireless ultrasound probe is positioned in the probe cup 202 such that the rechargeable element is in alignment with the core charger 204 and is being charged, a first light may be emitted to indicate the probe is cool and charging. For example, the LED 422 may blink green. In some examples, the core charger 204 may be configured to detect a temperature of the core charger 204 and/or of the wireless ultrasound probe. When the core charger 204 detects that at least one of the core charger 204 and/or of the wireless ultrasound probe exceeds a desired charging temperature, charging may be paused and the light emitted by the LED 422 may change to from the first light to the second light to indicate the probe is not charging and is hot. For example, light emitted by the LED 422 may change from blinking green to blue. When the core charger 204 and/or of the wireless ultrasound probe achieves the desired temperature (e.g., by passive and/or directed air circulation, as described herein), the light may change back to the first light (e.g., blinking green). When charging of the wireless ultrasound probe is sufficient for probe use, the LED 422 may emit a third light to indicate the probe is charged. For example, the third light may be continuous blue. If the core charger 204 is unable to charge the wireless ultrasound probe, for example, because the rechargeable element is not aligned with the charging element of the core charger 204 or the core charger 204 is otherwise unable to provide charge, the LED 422 may emit a fourth light. For example, the fourth light may be continuous orange. As described herein, each of the first light, the second light, the third light, and the fourth light may be different, and/or some of the lights may be the same, to indicate different charging states. Thus, the core charger 204 may visually indicate a charging status of the wireless ultrasound probe, which may increase a simplicity of charging.

Figure 5:
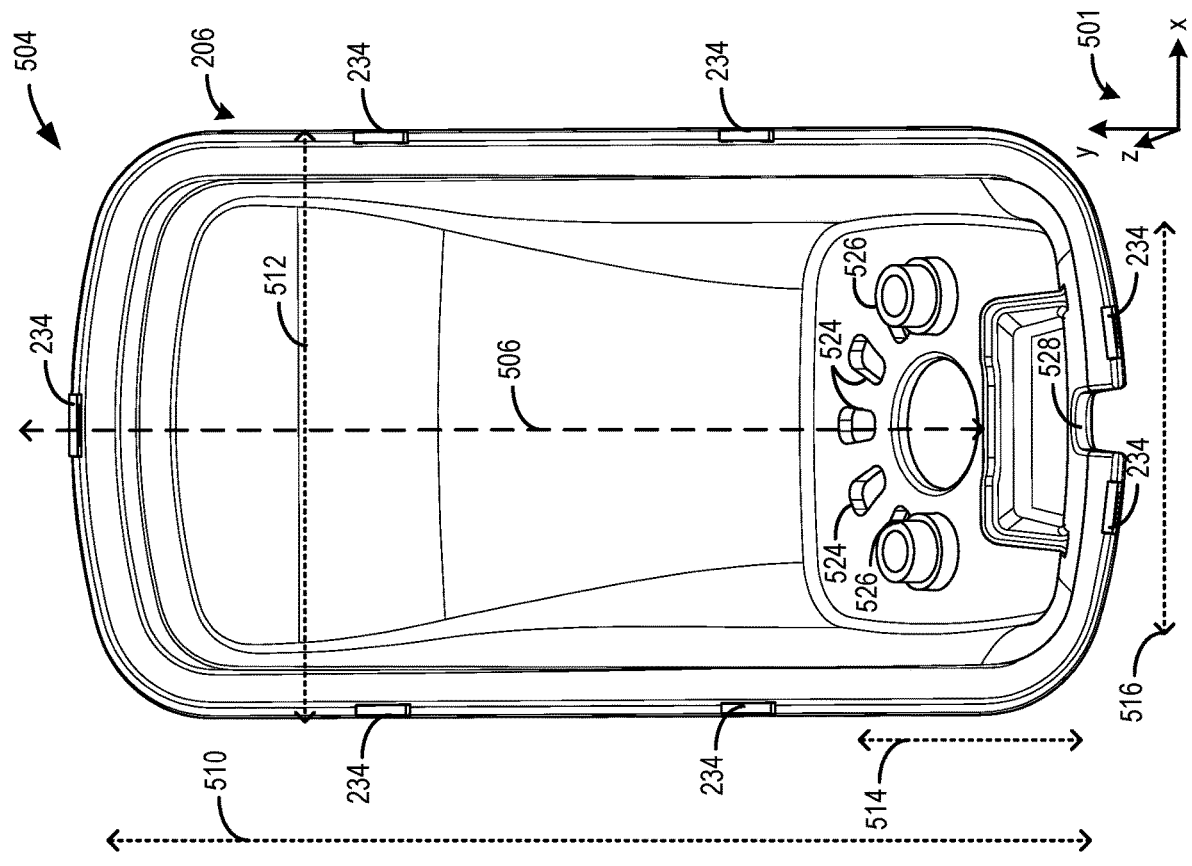
FIG. 5 shows a plurality of views of a body attachment of the charging system of FIG. 2.
Figure 5:
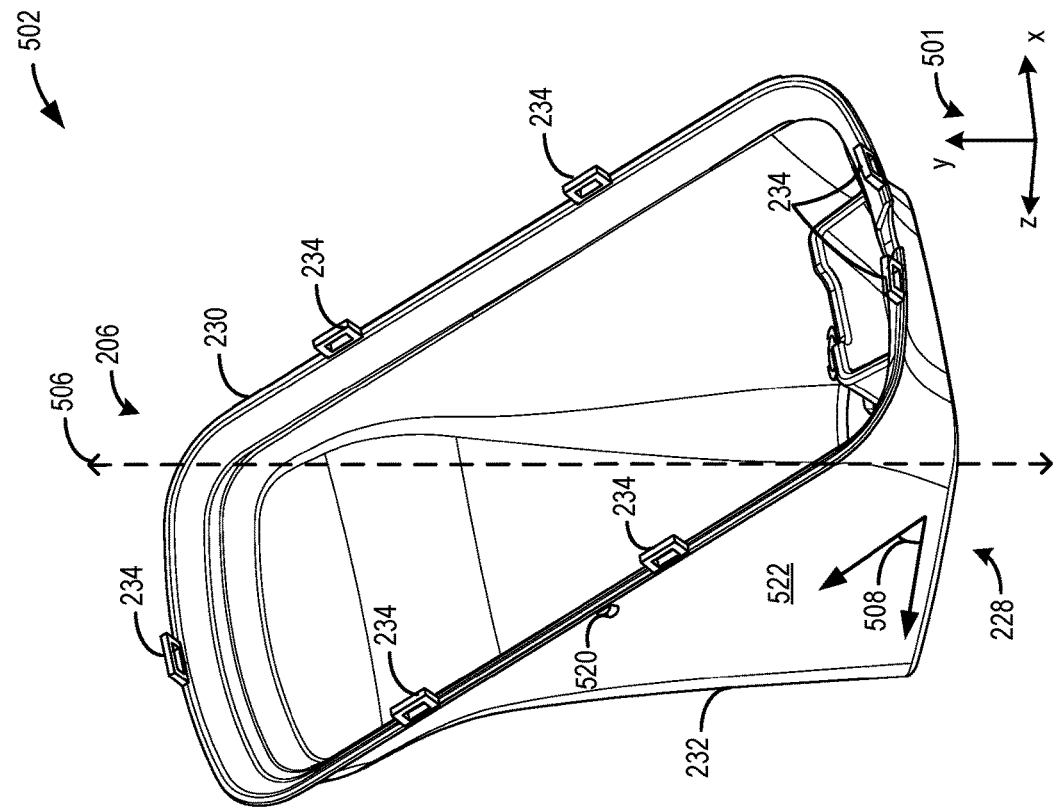

Turning to FIG. 5, a front right perspective view 502 and an angled perspective view 504 of the base attachment 206 are shown. An axis system 501 is provided in FIG. 5 for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples. Each of the views of FIG. 5 are herein described simultaneously.

As described with respect to FIG. 2, the base attachment 206 includes the bottom face 228, the angled face 230, and the hollow body 232. The hollow body 232 extends upwards from and continuous with the bottom face 228 (e.g., in a direction parallel to the y-axis, with respect to the axis system 501). The hollow body 232 flares outward from a central axis 506 of the hollow body 232 to form the angled face 230. The angled face 230 is angled 508 with respect to the bottom face 228, for example, at a 45-degree angle. Additionally, a length 510 and a width 512 of the angled face 230 may be greater than a base length 514 and a base width 516 of the bottom face 228. Dimensions of the angled face 230 may be similar to dimensions of the rear housing 414 of the core charger 204. As described with respect to FIG. 2, the angled face 230 may describe a perimeter of the hollow body 232 which is angled with respect to the bottom face 228. Described another way, the angled face 230 may be an angled plane. The plurality of clip extensions 234 extend from the angled face 230 in a direction perpendicular the angled face 230. Each of the plurality of clip extensions 234 may be positioned and sized to be complementary to each of the plurality of clip receivers 410 of the core charger 204.

As described herein, the core charger 204 is coupled to the base attachment 206 by snap fitting the plurality of clip extensions 234 into the plurality of clip receivers 410 and sliding the probe cup 202 over the first end 220 of the core charger 204 and the base attachment 206. The base attachment 206 may further include at least one protrusion 520 on a first side 522 of the flared out portion of the hollow body 232 and at least one protrusion (not shown) on a second side of the flared out portion of the hollow body 232, opposite the first side 522. Each of the at least one protrusion may be complementary in size, shape, and position to each of at least one indentation 332 of a probe cup (e.g., as shown in FIG. 3A) so as to provide a snap-fit latching connection between the probe cup 202 and the base attachment 206, with the core charger 204 positioned therebetween.

In some examples, the bottom face 228 of the base attachment 206 includes a plurality of vent slots 524. The plurality of vent slots 524 of the base attachment 206 may be similar in size, shape, and position to the plurality of vent slots 240 of a mounting attachment, such as the rim 236 of the mounting post 210 of the mounting attachment 208 of FIG. 2. The plurality of vent slots 524 may allow passive and/or directed air flow through the hollow body 232, which may enable cooling of the core charger 204. Additionally, the bottom face 228 may include passages 526 into which screws or other fasteners may be threaded to couple a mounting attachment (e.g., the mounting post 210) to the base attachment 206 and thus to the charging system 200. The bottom face 228 may further include a port housing 528 which is complementary to the opening 416 at the second end 418 of the core charger 204. In the example shown in FIG. 5, the port housing 528 includes a cutout 328 which may allow the charging cable 214 to extend through the base attachment 206 when the charging cable 214 is plugged into the charging port 604 of the core charger 204.

Returning to FIG. 6, in some examples of the charging system 200, a fan 608 may be positioned in the hollow body 232 of the base attachment 206. For example, the fan 608 may be positioned in the region of the hollow body 232 which extends upwards from and continuous with the bottom face 228 (e.g., in a direction parallel to the y-axis, with respect to the axis system 501) prior to flaring outward. The fan 608 may be mounted on the rear housing 414 of the core charger 204, for example, adjacent to but not covering the opening 416 into which the charging cable 214 is inserted. The fan 608 may intake air through the plurality of vent slots 524 of the bottom face 228 of the base attachment 206 and, when coupled to the bottom face 228, the plurality of vent slots 240 of a mounting attachment. The fan 608 may circulate air through the hollow body 232 of the base attachment 206 to cool the core charger 204.

Figure 7A:
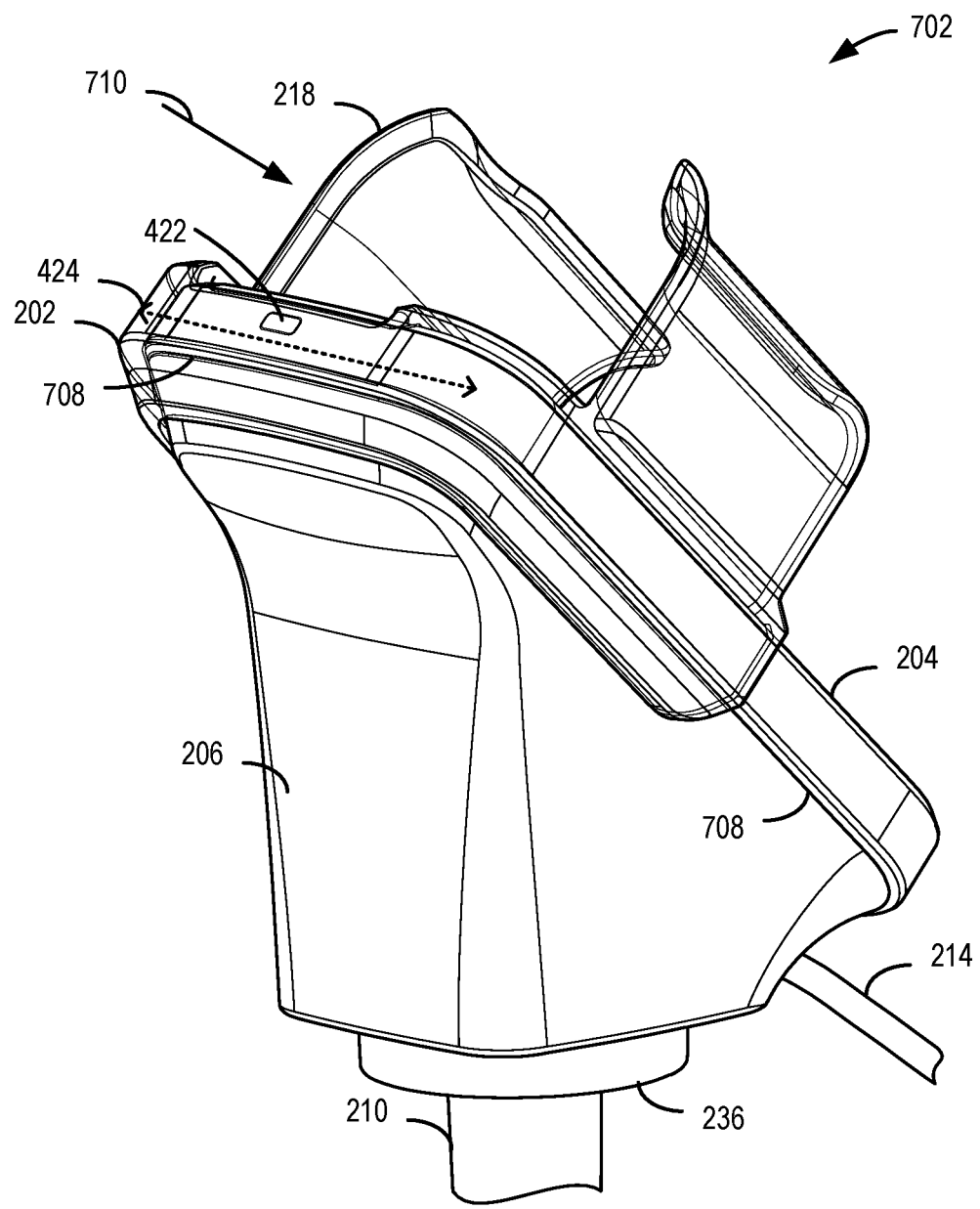
FIG. 7A shows a first views of the charging system and mounting attachment of FIG. 2 in an assembled configuration.
Figure 7B:
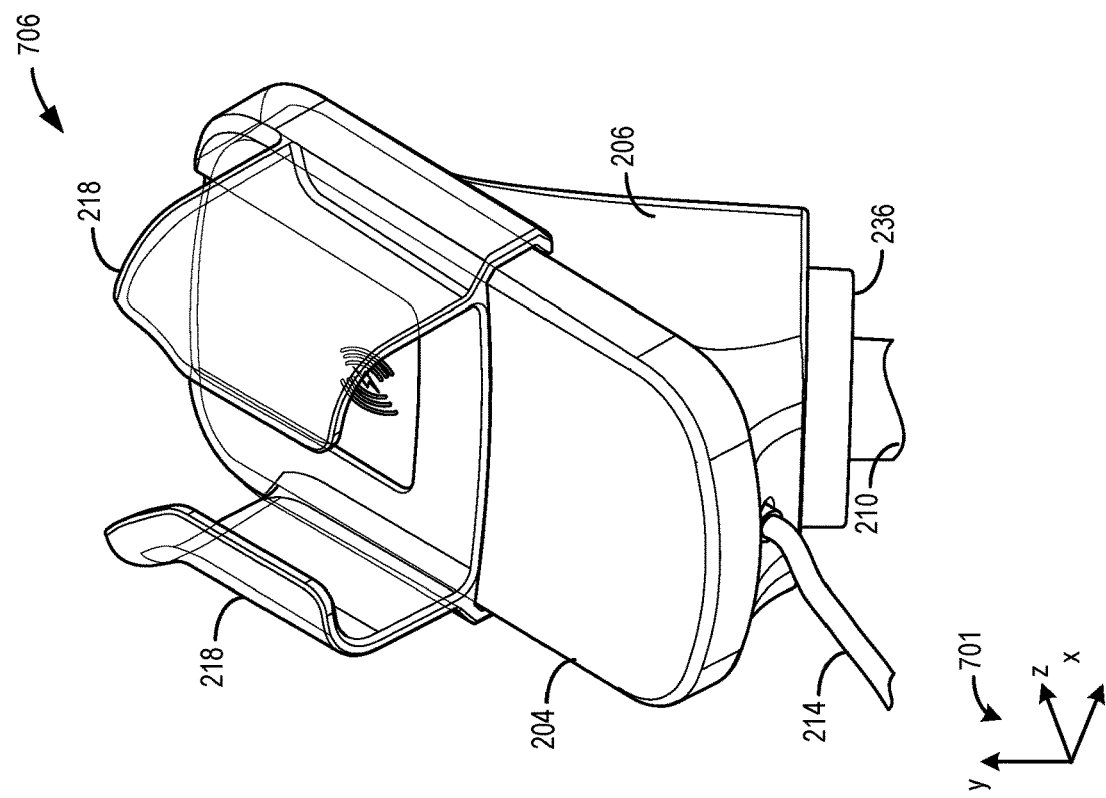
FIG. 7B shows a plurality of views of the charging system and mounting attachment of FIG. 2 in the assembled configuration.
Figure 7B:
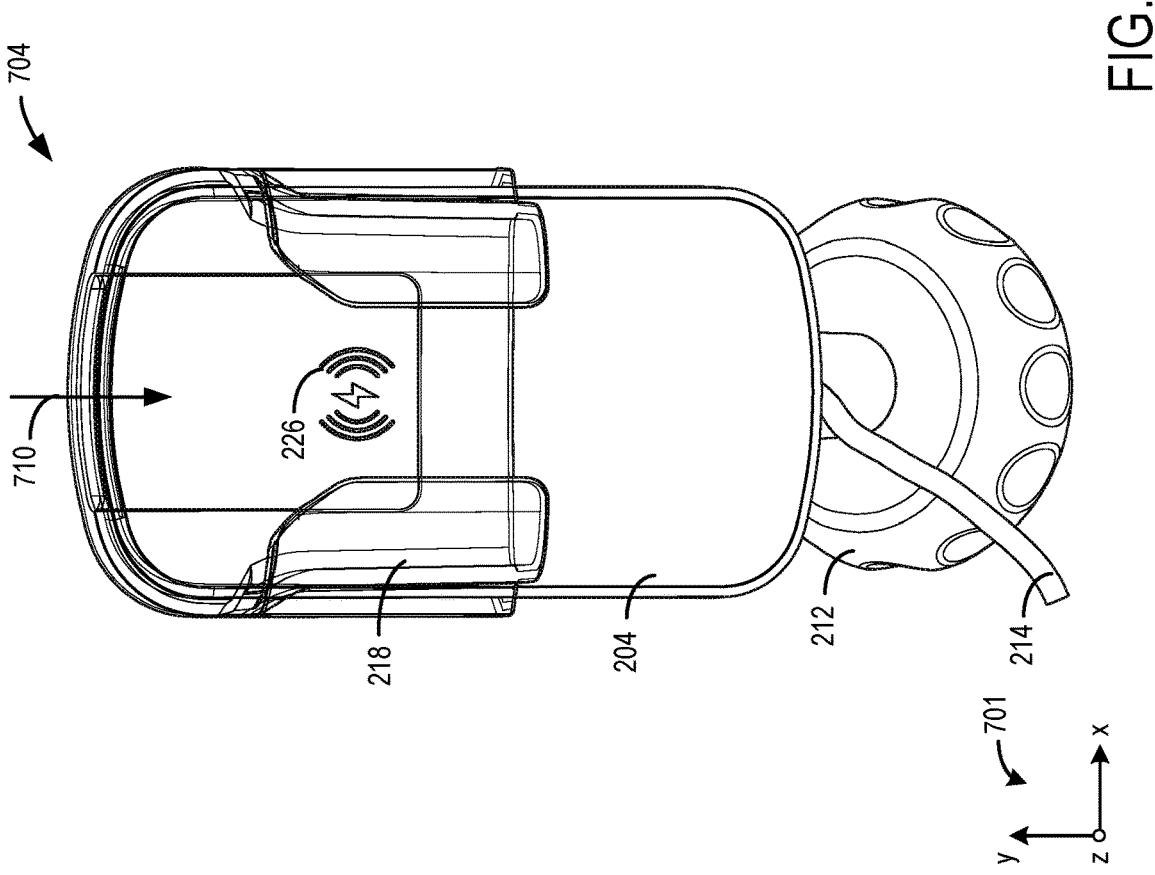

Turning to FIGS. 7A-7B, a plurality of views of the assembled charging system 200 are shown, including a back right perspective view 702, a front view 704, and a front left perspective view 706. An axis system 701 is provided in FIGS. 7A-7B for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples. Each of the views of FIGS. 7A-7B are herein described simultaneously.

The core charger 204 is coupled to the angled face 230 of the base attachment 206, such that the rear housing 414 of the core charger 204 extends into the hollow body 232 of the base attachment 206. Coupling of the core charger 204 and the base attachment 206 by snap fitting the plurality of clip extensions 234 into the plurality of clip receivers 410 (as described with respect to FIGS. 2, 4, and 5), forms an interface seam 708 between the core charger 204 and the base attachment 206. The probe cup 202 is coupled to the core charger 204 and the base attachment 206 by sliding the first bracket 216 of the probe cup 202 over the first end 220 of the core charger and base attachment 206. A curvature of the first bracket 216 may surround the width 424 of the core charger 204 and further surround the flared out portion of the base attachment 206. In this way, the probe cup may cover the interface seam 708 between the core charger 204 and the base attachment 206, which may prevent debris such as dust and/or fluids (e.g., biofluids, cleaning agents, ultrasound jelly, etc.) from entering the hollow body 232 of the base attachment 206 through the interface seam 708. Further, when the probe cup 202 is formed of transparent material, the LED 422 of the core charger 204 may be visualized through the transparent material of the probe cup 202.

A wireless ultrasound probe may slide into the second bracket 218 of the probe cup 202 in a direction shown by an arrow 710. As described with respect to FIG. 2, the core charger 204 may have the charging symbol 226 on the first surface 222 indicating a relative position of the charging element along the first surface 222. The cutout 328 of the first bracket 216 is positioned on the core charger 204 such that the charging symbol 226 is visible. When positioned in the probe cup 202 (e.g., in the second bracket 218), a battery of the wireless ultrasound probe may be aligned with the charging symbol 226 and therefore with the charging element of the core charger 204, enabling charging of the battery via inductive charging (e.g., wireless charging). The wireless ultrasound probe may be maintained in the aligned position by gravity and the second bracket 218 of the probe cup 202.

Figure 8:
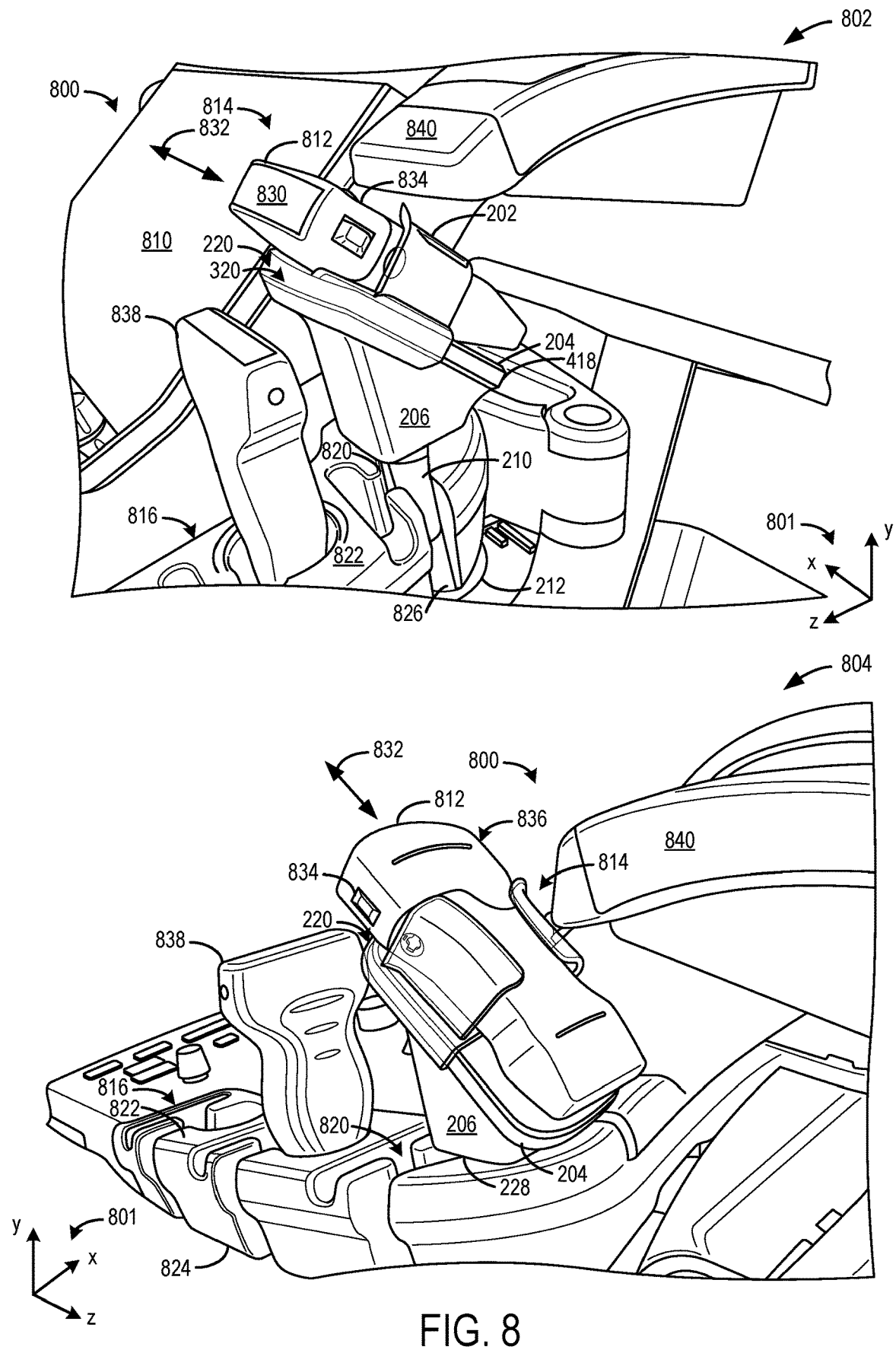
FIG. 8 shows perspective views of a first arrangement of the charging system and mounting attachment in a coupled configuration mounted to an ultrasound imaging system.

A mounting attachment may be coupled to the charging system 200 to enable mounting of the charging system 200 on an element of an ultrasound system, such as the system 100 of FIG. 1. As briefly described with respect to FIGS. 2 and 7, the mounting attachment 208 includes the mounting post 210 and the lock nut 212. Turning to FIG. 8, the charging system 200 coupled to the mounting attachment 208 is shown in a first perspective view 802 and a second perspective view 804, where the mounting attachment 208 is used to mount the charging system 200 to an ultrasound imaging console 800. An axis system 801 is provided in FIG. 8 for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples. Each of the views of FIG. 8 are herein described simultaneously.

The ultrasound imaging console 800 may be an example of the ultrasound imaging system (e.g., the system 100) of FIG. 1. The ultrasound imaging console 800 may be a cart with wheels so that the ultrasound imaging console 800 may be portable and be moved throughout an area, such as around or between patient rooms in a healthcare provider office. The ultrasound imaging console 800 includes a display 810 which is in electronic communication with a controller of the ultrasound imaging console 800. For example, the display 810 may be the display device 118 and the controller may be the system controller 116 of FIG. 1. The ultrasound imaging console 800 may further include memory and processors, as described with respect to the system 100 of FIG. 1.

A wireless ultrasound probe 812 is also in wireless electronic communication with the controller of the console and may be positioned in a wireless charging assembly 814 configured to wirelessly charge a power source of the wireless ultrasound probe 812. The wireless ultrasound probe 812 may be an example of the diagnostic ultrasound probe 106 (or transducer) of FIG. 1. The power source of the wireless ultrasound probe 812 may be, for example, a rechargeable battery, as described with respect to FIGS. 2-7. The wireless charging assembly 814 is an example of the charging system 200 coupled to the mounting attachment 208 of FIGS. 2-7. Elements of the wireless charging assembly 814 and the mounting attachment 208 will be described with respect to the charging system 200.

The wireless charging assembly 814 includes a mounting attachment (e.g., the mounting attachment 208), a base attachment (e.g., the base attachment 206) configured to be attached to the mounting attachment 208, a core charger (e.g., the core charger 204) configured to be attached to the base attachment 206 and further to charge the wireless ultrasound probe 812 via inductive charging, and a probe cup (e.g., the probe cup 202). As described with respect to FIGS. 2 and 5, the base attachment 206 may be coupled to the mounting post 210 of the mounting attachment 208 by threading at least one screw though passages of the mounting post 210 and the base attachment 206. In other examples, the base attachment 206 may be coupled to the mounting attachment 208 via clip, screw, threading, and/or other fastening methods.

The ultrasound imaging console 800 includes a housing enclosing the display 810 and the controller. The housing further includes a storage section 816 having a first storage 820 which extends between a first storage section surface 822 and a second storage section surface 824, opposite the first storage section surface 822. The mounting attachment 208 is configured to releasably couple the wireless charging assembly 814 to the ultrasound imaging console 800. As described with respect to FIG. 8, the mounting attachment 208 is configured to releasably couple the wireless charging assembly 814 to the first storage 820 of the storage section 816 of the ultrasound imaging console 800. In other examples, a different mounting attachment may be used to releasably couple the wireless charging assembly 814 to other elements of a medical device, such as a handle of an ultrasound cart, a pole of a patient monitor, and/or a piece of user-worn equipment. As described with respect to FIG. 8, mounting post 210 may extend through the first storage 820 and, in some examples, the bottom face 228 of the base attachment 206 may rest on (e.g., be in face-sharing contact with) the first storage section surface 822 around the first opening 312. The lock nut 212 may be threaded or otherwise coupled to the mounting post 210, as described above, to secure the mounting attachment 208 and therefore the wireless charging assembly 814 in the first opening 312. For example, at least a portion of a first lock nut face 826 of the lock nut 212 may be in face-sharing contact with the second storage section surface 824.

The wireless charging assembly 814 may be oriented in such a way that the first end 220 of the core charger 204 and the top 320 of the first bracket 216 of the probe cup 202 face a same direction as the display 810 of the ultrasound imaging console 800, such as towards a user of the ultrasound imaging console 800. Described another way, the first end 220 of the core charger 204 and the top 320 of the first bracket 216 of the probe cup 202 are a greater distance from the first storage section surface 822 than the second end 418 of the core charger 204. When the wireless ultrasound probe 812 is positioned in the probe cup 202, a scanning element 830 of the wireless ultrasound probe 812 may face the same direction as the display 810 of the ultrasound imaging console 800. In this way, when the wireless ultrasound probe 812 is removed from the probe cup 202, the wireless ultrasound probe 812 may be positioned in an orientation used for ultrasound scans. For example, the wireless ultrasound probe 812 may be removed from the probe cup 202 in a first direction 832 parallel to the first surface 222 of the core charger 204, where a user may grasp the wireless ultrasound probe 812 on a first side 834 and a second side 836 of the wireless ultrasound probe 812 using one hand. The user may rotate the wireless ultrasound probe 812 approximately 180-degrees by switching a position of their hand, for example, removing the wireless ultrasound probe 812 in the first direction 832 where the scanning element 830 faces towards the user, and rotating the wrist so that the scanning element 830 faces away from the user.

Additionally, the angle of the base attachment 206 and thus the angle of the core charger 204 when coupled to the base attachment 206, the probe cup 202 coupled to the core charger 204 and the base attachment 206, and the wireless ultrasound probe 812 when positioned in the probe cup 202 is such that insertion and removal of the wireless ultrasound probe 812 into and out of the wireless charging assembly 814 may have clearance between additional elements of the ultrasound imaging console 800. For example, the wireless ultrasound probe 812 may be removed from the probe cup 202 without being navigated around a second probe 838 and a warming pad 840 for ultrasound gel which may be used with the wireless ultrasound probe 812.

Figure 9:
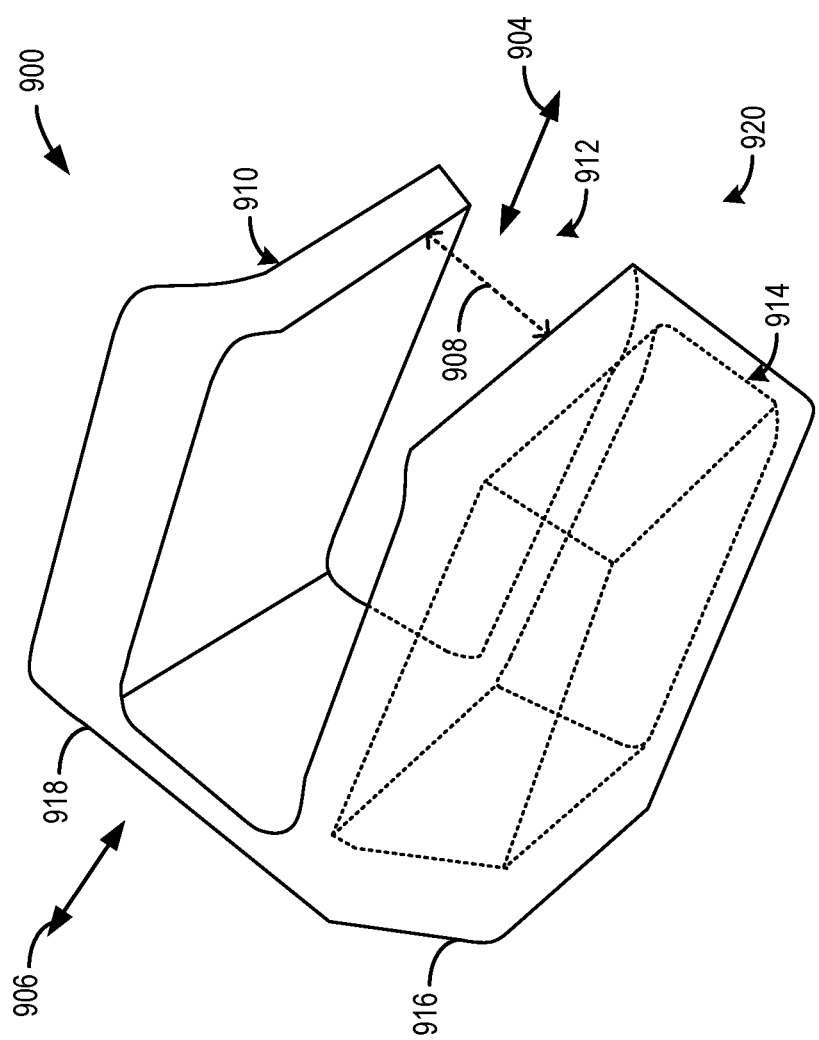
FIG. 9 shows a probe clip of a charging system, according to an embodiment of the disclosure.

As described herein, a charging system for a wireless ultrasound probe may include different types of probe holders which are configured to retain and position a wireless ultrasound probe adjacent to the charging element of the core charger 204, enabling inductive charging of the rechargeable element of the wireless ultrasound probe. FIG. 9 shows a second example probe holder formed as a probe clip 900. The probe clip 900 may be used to position and retain the wireless ultrasound probe 812, however the probe clip 900 may be configured to additionally or alternatively position and retain wireless ultrasound probes having different shapes and/or sizes.

The probe clip 900 may be similarly configured to the probe cup 202 and have a first bracket 916 and a second bracket 918. The first bracket 916 and the second bracket 918 may together form a continuous body of the probe clip 900. The first bracket 916 includes an opening 914 on a bottom 920 of the probe clip 900, wherein the opening 914 is configured to slide over the first end 220 of the core charger 204 and the base attachment 206. Dashed lines in the first bracket 916 indicate a space in which the core charger 204 and the base attachment 206 may be positioned. The second bracket 918 may have a c-shape, where the c-shape extends from the first bracket 916 and a side 912 of the second bracket is open (e.g., non-continuous with the first bracket 916). For example, a front 910 of the second bracket 918 may be spaced away from the first bracket 916 by a distance 908. As further described with respect to FIG. 10, the probe clip 900 may be configured such that a wireless ultrasound probe (e.g., the wireless ultrasound probe 812) may be inserted into and removed from the second bracket 918 in a second direction 906 and/or a third direction 904. For example, the second direction 906 may be parallel to the first surface 222 of the core charger 204 and the third direction 904 may be parallel to the width 424 of the core charger 204.

Figure 10:
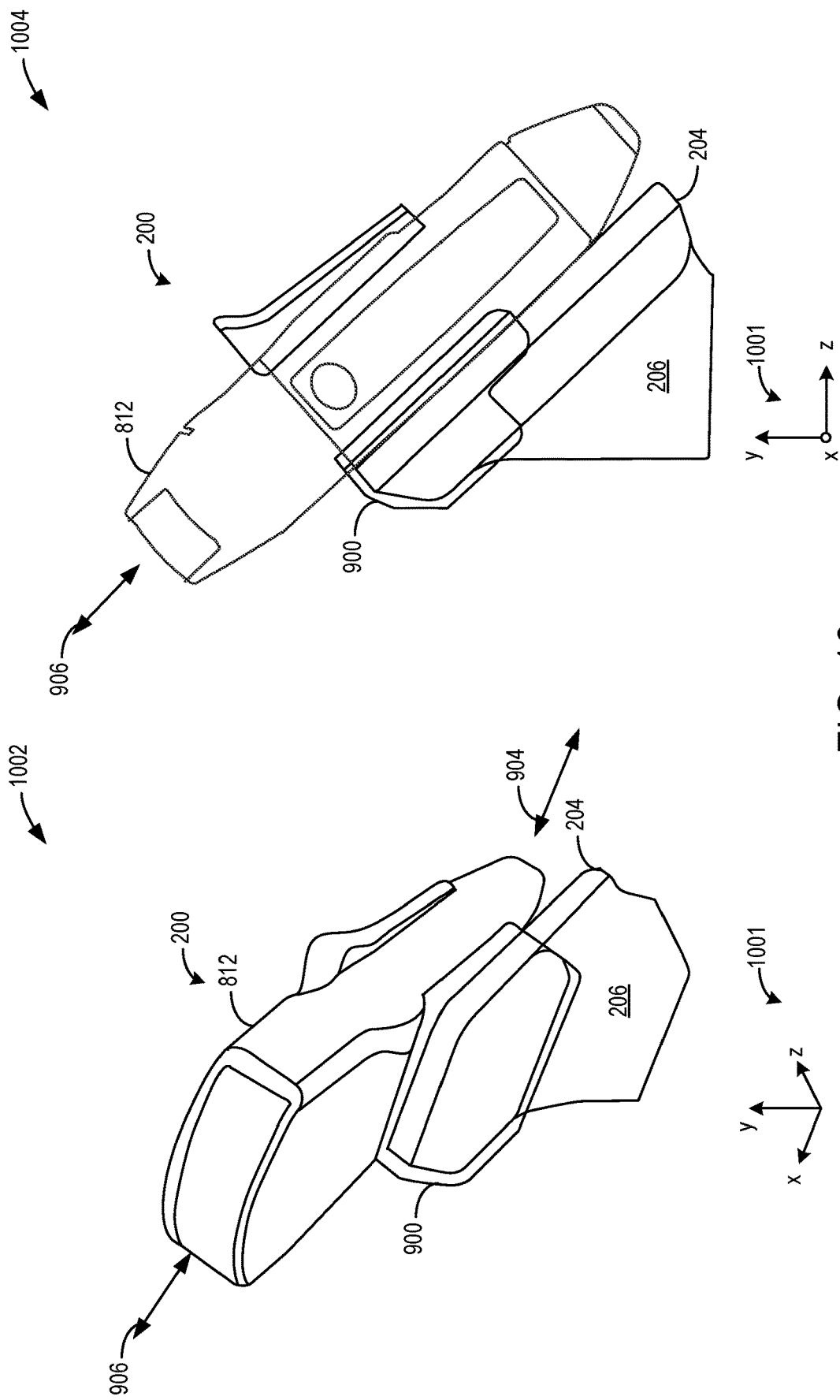
FIG. 10 shows perspective views of a second arrangement of the charging system and mounting attachment in a coupled configuration, according to an embodiment of the disclosure.

Turning to FIG. 10, the probe clip 900 is shown in place of the probe cup 202 in the charging system 200. Other elements of the charging system 200 are as described with respect to FIGS. 2-8, and some elements may not be reintroduced herein for brevity. An axis system 1001 is provided in FIG. 10 for reference. The y-axis may be a vertical axis (e.g., parallel to a gravitational axis), the x-axis may be a lateral axis (e.g., a horizontal axis), and the z-axis may be a longitudinal axis, in one example. However, the axes may have other orientations in other examples. In both a right rear perspective view 1002 and a right side view 1004 of FIG. 10, the probe clip 900 is shown as transparent so that the core charger 204 and the base attachment 206 may be visualized in the first bracket 916. As described with respect to the probe cup 202, the probe clip 900 may also be formed of non-transparent material and otherwise configured to display the LED 422 of the core charger 204 to indicate the charging state of the wireless ultrasound probe 812. Whereas the wireless ultrasound probe 812 may be inserted into and removed from the probe cup 202 in the first direction 832 and retained in the probe cup 202 by gravity, the wireless ultrasound probe 812 may be inserted into and removed from the probe clip 900 in both the second direction 906 and the third direction 904 and retained in the probe clip 900 by both gravity and tension of the probe clip 900. For example, the wireless ultrasound probe 812 may be inserted into the probe clip 900 by pulling or otherwise adjusting the front 910 of the second bracket 918 away from the first bracket 916 in a direction perpendicular to the first surface 222 of the core charger 204 (e.g., parallel to the z-axis, with respect to the axis system 1001), inserting the wireless ultrasound probe 812 into the side 912 of the second bracket 918 (e.g., in the third direction 904, parallel to the x-axis with respect to the axis system 1001), and releasing the second bracket 918. Temporarily increasing the distance 908 between the first bracket 916 and the second bracket 918 may allow the wireless ultrasound probe 812 to be inserted into the probe clip 900. When the front 910 is released, a distance between the first bracket 916 and the second bracket 918 may return to approximately the distance 908 to retain the wireless ultrasound probe 812 in the probe clip 900.

Additionally, the charging system 200 may be coupled to different mounting attachments which may be configured to couple the charging system 200 to different elements of a medical imaging system. For example, a different mounting attachment may be used to releasably couple the charging system 200 to elements such as a handle of an ultrasound cart, a pole of a patient monitor, and/or a piece of user-worn equipment. The different mounting attachments described herein may be coupled to the base attachment 206 similarly to coupling of the mounting post 210 to the base attachment 206 (e.g., by threading screws through passages of the rim 236 and the bottom face 228). In some examples, a vice grip and/or clamp may be the mounting attachment used to releasably couple the charging system 200 to a vertical extension of a medical imaging system, such as a pole of a patient monitor stand. A c-clip may be an example of a mounting attachment used to releasably couple the charging system 200 to a handle or other horizontal extension of a medical imaging system. For example, the c-clip may at least partially surround an interior and exterior of the handle such that a portion of the c-clip rests on a top of the handle and is held in place by gravity. In further examples, clip-in devices may be used as a mounting attachment to couple the charging system 200 to user-worn equipment, such as a vest, harness, belt, and so on of a care provider.

The charging system thus provides a modular system which may be used to charge a rechargeable probe of a medical device. A method for charging the rechargeable probe using the charging system is described with respect to FIGS. 2-10. As described herein, the charging system is used with an ultrasound imaging system to recharge a wireless ultrasound probe. A shape, size, dimensions, and so on of the charging system may be adapted to perform the functions described herein for probes having different sizes and shapes. Assembling the modular system may include, in some examples, coupling the core charger to the base attachment by snap fitting clip extensions of the base attachment into clip receivers of the core charger. The probe holder may be coupled to the core charger by sliding the first bracket of the probe holder over the upper region of the core charger and the base attachment, coupled to the core charger. The rechargeable probe is positioned in the probe holder by inserting the probe into the second bracket of the probe holder. When positioned in the probe holder, the rechargeable element (e.g., battery) of the rechargeable probe is aligned with the rechargeable element of the core charger and the rechargeable probe is retained in the probe holder. For example, as described with respect to FIGS. 3A-3B and 7-8, when the probe holder is a probe cup, the rechargeable probe may be inserted into the probe cup in a direction parallel to the first surface of the core charger. In other examples where the probe holder is a probe clip, such as described with respect to FIGS. 9-10, the rechargeable probe may be inserted into the probe clip in a direction parallel to the first surface of the core charger and/or inserted from a side of the probe clip (e.g., in a direction parallel to an x-axis).

The core charger and the probe holder are configured to enable visualization of the charging state of the rechargeable probe. For example, the core charger may output a first light when the rechargeable probe is positioned in the probe holder such that the rechargeable element is in alignment with the core charger and is being charged via inductive charging. The first light may be emitted to indicate the rechargeable probe is at or below a desired temperature, where the desired temperature is desired for efficient rechargeable probe charging. When the core charger detects that at least one of the core charger and/or of the probe exceeds the desired temperature, charging may be paused. The core charger may output a second light to indicate the probe is not charging and a temperature of the probe is greater than the desired temperature. When charging of the probe is sufficient for probe use, the core charger may emit a third light to indicate the probe is charged. If the core charger is unable to charge the probe, for example, because the rechargeable element is not aligned with the charging element of the core charger or the core charger is otherwise unable to provide charge, the core charger may emit a fourth light.

Further, the charging system may be coupled to a mounting attachment and be mounted on an ultrasound imaging system (e.g., as shown in the wireless charging assembly 814). The core charger, the base attachment, and the probe holder (e.g., together, the charging system) may be removably coupled to a mounting attachment via the base attachment using snap fit elements, threaded fasteners, and/or other fastening methods. The mounting attachment may be used to mount the charging system on an element of the medical device (e.g., a handle of a portable ultrasound cart, a pole of a patient monitor, a piece of user-worn equipment, etc.) via a clamp, clip, and/or grip of the mounting attachment, for example.

In this way, a charging system for a wireless ultrasound probe of an ultrasound imaging system may be configured to be modular. Different probe holders may be coupled to a core charger and a base attachment to enable positioning and retention of different wireless ultrasound probes on the core charger. The core charger, base attachment, and probe holders may be coupled to each other using features of the respective elements and without additional fasteners, thus increasing a simplicity of the charging system with respect to conventional charging systems. The base attachment may be coupled to different mounting attachments to mount the charging system on different elements of the ultrasound imaging system.

FIGS. 2-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The disclosure also provides support for a charging system for a wireless ultrasound probe, comprising: a base attachment configured to be removably coupled to an ultrasound system, a core charger configured to be removably coupled to the base attachment, wherein the core charger is configured to charge the wireless ultrasound probe via inductive charging, and a probe holder comprising a first bracket and a second bracket, wherein the first bracket is configured to be removably coupled to the core charger, wherein the second bracket is configured to receive the wireless ultrasound probe and position the wireless ultrasound probe adjacent to the core charger to enable charging of the wireless ultrasound probe via inductive charging. In a first example of the system, the base attachment includes: a bottom face configured to removably couple to a mounting attachment, an angled face configured to removably couple to the core charger, the angled face positioned at a non-zero angle relative to the bottom face, and a body extending between the bottom face and the angled face, wherein the body is a hollow cup where the bottom face is a solid base continuous with the body and the angled face is a perimeter of the body. In a second example of the system, optionally including the first example, the base attachment includes a plurality of clip extensions positioned around and extending perpendicular from the angled face of the base attachment, the plurality of clip extensions configured to be snap fit into clip receivers of the core charger. In a third example of the system, optionally including one or both of the first and second examples, the base attachment includes a fan positioned in the body of the base attachment and angled at the angle of the angled face. In a fourth example of the system, optionally including one or more or each of the first through third examples, the core charger includes a plurality of clip receivers positioned around a perimeter of a second surface of the core charger, the plurality of clip receivers configured to receive clip extensions of the base attachment. In a fifth example of the system, optionally including one or more or each of the first through fourth examples, the core charger includes an LED at a first end of the core charger, the LED configured to indicate a charging status of the wireless ultrasound probe when positioned on the core charger. In a sixth example of the system, optionally including one or more or each of the first through fifth examples, the core charger includes edge lighting. In a seventh example of the system, optionally including one or more or each of the first through sixth examples, the core charger includes a charging port at a second end of the core charger into which a charging cable is inserted to provide the core charger with power. In an eighth example of the system, optionally including one or more or each of the first through seventh examples, the core charger includes a charging element in an upper region of the core charger. In a ninth example of the system, optionally including one or more or each of the first through eighth examples, the probe holder is formed of transparent material. In a tenth example of the system, optionally including one or more or each of the first through ninth examples, the first bracket has a stepped configuration to create a standoff distance between a charging surface of the core charger and a front face of the probe holder when the probe holder is coupled to core charger.

The disclosure also provides support for an ultrasound imaging system, comprising: an ultrasound imaging console comprising a controller in electronic communication with a display, a wireless ultrasound probe in wireless electronic communication with the controller, and a wireless charging assembly configured to wirelessly charge a power source of the wireless ultrasound probe, the wireless charging assembly including: a mounting attachment configured to releasably couple the wireless charging assembly to the ultrasound imaging system, a base attachment having a bottom face and an angled face, the bottom face configured to be attached to the mounting attachment, a core charger configured to be attached to the base attachment, wherein the core charger is configured to charge the wireless ultrasound probe via inductive charging, and a probe holder comprising a first bracket and a second bracket, wherein the first bracket is configured to be removably coupled to the core charger, wherein the second bracket is configured to receive the wireless ultrasound probe and position the wireless ultrasound probe adjacent to the core charger to enable charging of the wireless ultrasound probe via inductive charging. In a first example of the system, the base attachment is coupled to the mounting attachment via a clip, a screw, a threading, or other fastener. In a second example of the system, optionally including the first example, the mounting attachment includes a clamp, a mounting post, and/or a C-clip. In a third example of the system, optionally including one or both of the first and second examples, the ultrasound imaging console includes a housing enclosing the display, the controller, and a storage section having a first storage extending between a first surface of the storage section and a second surface of the storage section opposite the first surface. In a fourth example of the system, optionally including one or more or each of the first through third examples, the mounting attachment is configured to releasably couple the wireless charging assembly to the first storage of the storage section. In a fifth example of the system, optionally including one or more or each of the first through fourth examples, releasably coupling the wireless charging assembly to the ultrasound imaging system via the mounting attachment includes releasably coupling the wireless charging assembly to a handle, a stand, a pole, and/or user-worn equipment.

The disclosure also provides support for a method for charging a rechargeable probe of a medical device, comprising: releasably coupling a core charger to a base attachment by snap fitting clip extensions of the base attachment to clip receivers of the core charger, releasably coupling a probe holder to the core charger by sliding a first bracket of the probe holder over an upper region of the core charger and the base attachment, positioning the rechargeable probe in the probe holder by inserting the rechargeable probe into a second bracket of probe holder such that a battery of rechargeable probe is aligned with a charging element of the core charger. In a first example of the method, the method further comprises: releasably coupling the core charger, the base attachment, and the probe holder to a mounting attachment at the base attachment using snap fit elements, threaded fasteners, and/or other fastening methods, and releasably mounting the mounting attachment on an element of the medical device via a clamp, clip, and/or grip of the mounting attachment. In a second example of the method, optionally including the first example, the method further comprises: indicating a charging state of the rechargeable probe using the core charger by: outputting a first light when the rechargeable probe is being charged by the core charger via inductive charging and the rechargeable probe is at or below desired temperature, outputting a second light when rechargeable probe is not charging and/or is above the desired temperature, outputting a third light when the rechargeable probe is charged, and outputting a fourth light when the core charger is unable to provide charge to the rechargeable probe.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A charging system for a wireless ultrasound probe, comprising:
   a base attachment configured to be removably coupled to an ultrasound system;
   a core charger configured to be removably coupled to the base attachment, wherein the core charger is configured to charge the wireless ultrasound probe via inductive charging; and
   a probe holder comprising a first bracket and a second bracket, wherein the first bracket is configured to be removably coupled to the base attachment and the core charger, wherein the second bracket is configured to receive the wireless ultrasound probe and position the wireless ultrasound probe adjacent to the core charger to enable charging of the wireless ultrasound probe via inductive charging,
   wherein the second bracket includes a first arm and a second arm, each of the first arm and the second arm being inset from lateral edges of the probe holder, and an outward flare of each of the first arm and the second arm being shaped complementary to a curvature of the wireless ultrasound probe.

2. The charging system of claim 1, wherein the base attachment includes:
a bottom face configured to removably couple to a mounting attachment;
an angled face configured to removably couple to the core charger, the angled face positioned at a non-zero angle relative to the bottom face; and
a body extending between the bottom face and the angled face, wherein the body is a hollow cup where the bottom face is a solid base continuous with the body and the angled face is a perimeter of the body.

3. The charging system of claim 2, wherein the base attachment includes a plurality of clip extensions positioned around and extending perpendicular from the angled face of the base attachment, the plurality of clip extensions configured to be snap fit into clip receivers of the core charger.

4. The charging system of claim 2, wherein the base attachment includes a fan positioned in the body of the base attachment and angled at the angle of the angled face.

5. The charging system of claim 1, wherein the core charger includes a plurality of clip receivers positioned around a perimeter of a second surface of the core charger, the plurality of clip receivers configured to receive clip extensions of the base attachment.

6. The charging system of claim 1, wherein the core charger includes an LED at a first end of the core charger, the LED configured to indicate a charging status of the wireless ultrasound probe when positioned on the core charger.

7. The charging system of claim 1, wherein the core charger includes edge lighting.

8. The charging system of claim 6, wherein the core charger includes a charging port at a second end of the core charger into which a charging cable is inserted to provide the core charger with power.

9. The charging system of claim 1, wherein the core charger includes a charging element in an upper region of the core charger.

10. The charging system of claim 1, wherein the probe holder is formed of transparent material, and wherein the first bracket includes at least one indentation on an internal side of the first bracket, the at least one indentation being complementary in size, shape, and position to a protrusion of the base attachment.

11. The charging system of claim 1, wherein the first bracket has a stepped configuration to create a standoff distance between a charging surface of the core charger and a front face of the probe holder when the probe holder is coupled to core charger, and wherein the first bracket further includes a cutout extending from a top of the first bracket.

12. An ultrasound imaging system, comprising:
an ultrasound imaging console comprising a controller in electronic communication with a display;
a wireless ultrasound probe in wireless electronic communication with the controller; and
a wireless charging assembly configured to wirelessly charge a power source of the wireless ultrasound probe, the wireless charging assembly including:
a mounting attachment configured to releasably couple the wireless charging assembly to the ultrasound imaging system;
a base attachment having a bottom face and an angled face, the bottom face configured to be attached to the mounting attachment;
a core charger configured to be attached to the base attachment, wherein the core charger is configured to charge the wireless ultrasound probe via inductive charging; and
a probe holder comprising a first bracket and a second bracket, wherein the first bracket is configured to be removably coupled to the base attachment and the core charger, wherein the second bracket is configured to receive the wireless ultrasound probe and position the wireless ultrasound probe adjacent to the core charger to enable charging of the wireless ultrasound probe via inductive charging,
wherein the second bracket includes a first arm and a second arm, each of the first arm and the second arm being inset from lateral edges of the probe holder, and an outward flare of each of the first arm and the second arm being shaped complementary to a curvature of the wireless ultrasound probe.

13. The ultrasound imaging system of claim 12, wherein the base attachment is coupled to the mounting attachment via a clip, a screw, a threading, or other fastener.

14. The ultrasound imaging system of claim 12, wherein the mounting attachment includes a clamp, a mounting post, and/or a C-clip.

15. The ultrasound imaging system of claim 12, wherein the ultrasound imaging console includes a housing enclosing the display, the controller, and a storage section having a first storage extending between a first surface of the storage section and a second surface of the storage section opposite the first surface.

16. The ultrasound imaging system of claim 15, wherein the mounting attachment is configured to releasably couple the wireless charging assembly to the first storage of the storage section.

17. The ultrasound imaging system of claim 16, wherein releasably coupling the wireless charging assembly to the ultrasound imaging system via the mounting attachment includes releasably coupling the wireless charging assembly to a handle, a stand, a pole, and/or user-worn equipment.

18. A method for charging a rechargeable probe of a medical device, comprising:
releasably coupling a core charger to a base attachment by snap fitting clip extensions of the base attachment to clip receivers of the core charger;
releasably coupling a probe holder to the base attachment and the core charger by sliding a first bracket of the probe holder over an upper region of the core charger and the base attachment;
positioning the rechargeable probe in the probe holder by inserting the rechargeable probe into a second bracket of probe holder such that a battery of rechargeable probe is aligned with a charging element of the core charger,
wherein the second bracket of the probe holder includes a first arm and a second arm, each of the first arm and the second arm being inset from lateral edges of the probe holder, and an outward flare of each of the first arm and the second arm being shaped complementary to a curvature of the wireless ultrasound probe.

19. The method of claim 18, further comprising:
releasably coupling the core charger, the base attachment, and the probe holder to a mounting attachment at the base attachment using snap fit elements, threaded fasteners, and/or other fastening methods; and
releasably mounting the mounting attachment on an element of the medical device via a clamp, clip, and/or grip of the mounting attachment.

20. The method of claim 18, further comprising indicating a charging state of the rechargeable probe using the core charger by:

outputting a first light when the rechargeable probe is being charged by the core charger via inductive charging and the rechargeable probe is at or below desired temperature;

outputting a second light when rechargeable probe is not charging and/or is above the desired temperature;

outputting a third light when the rechargeable probe is charged; and outputting a fourth light when the core charger is unable to provide charge to the rechargeable probe.

* * * * *